United States Patent
Bradley et al.

(10) Patent No.: US 10,858,436 B2
(45) Date of Patent: Dec. 8, 2020

(54) PSGL-1 MODULATORS AND USES THEREOF

(71) Applicant: Sanford Burnham Prebys Medical Discovery Institute, La Jolla, CA (US)

(72) Inventors: Linda M. Bradley, La Jolla, CA (US); Roberto Tinoco, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 8 days.

(21) Appl. No.: 15/324,262

(22) PCT Filed: Jul. 8, 2015

(86) PCT No.: PCT/US2015/039586
§ 371 (c)(1),
(2) Date: Jan. 5, 2017

(87) PCT Pub. No.: WO2016/007653
PCT Pub. Date: Jan. 14, 2016

(65) Prior Publication Data
US 2017/0198047 A1    Jul. 13, 2017

Related U.S. Application Data

(60) Provisional application No. 62/022,191, filed on Jul. 8, 2014.

(51) Int. Cl.
| | | |
|---|---|---|
| *A61K 39/00* | (2006.01) |
| *A61K 39/002* | (2006.01) |
| *A61K 45/00* | (2006.01) |
| *C07K 16/28* | (2006.01) |
| *C07K 14/705* | (2006.01) |
| *A61K 48/00* | (2006.01) |

(52) U.S. Cl.
CPC .... *C07K 16/2854* (2013.01); *C07K 14/70596* (2013.01); *C07K 16/2896* (2013.01); *A61K 48/00* (2013.01); *A61K 2039/505* (2013.01); *C07K 2317/76* (2013.01)

(58) Field of Classification Search
CPC ........................ A61K 39/00; A61K 39/001102
USPC .................. 424/9.1, 9.2, 184.1, 243.1, 278.1
See application file for complete search history.

(56) References Cited

U.S. PATENT DOCUMENTS

| | | |
|---|---|---|
| 7,563,760 B2 | 7/2009 | Larsen et al. |
| 8,298,540 B2 * | 10/2012 | Lin .................... C07K 16/28 424/130.1 |
| 2002/0058034 A1 | 5/2002 | Manjunath et al. |
| 2005/0152906 A1 | 7/2005 | Levanon et al. |
| 2009/0304709 A1 | 12/2009 | Lin et al. |
| 2012/0014979 A1 | 1/2012 | Dent |

FOREIGN PATENT DOCUMENTS

| | | |
|---|---|---|
| CN | 1678348 A | 10/2005 |
| CN | 101045161 A | 10/2007 |
| CN | 101300021 A | 11/2008 |
| JP | 2004521958 A | 7/2004 |
| WO | WO-2016007653 A2 | 1/2016 |

OTHER PUBLICATIONS

Partial Supplementary European Search Report dated Oct. 27, 2017, regarding EP 15819318.5.
Zhang, S. et al.: "*Targeting CD162 protects against streptococcal M1 protein-evoked neutrophil recruitment and lung injury*"; Am J. Physiology—Lung Cellular and Molecular Physiology, vol. 305, No. 10, Nov. 15, 2013, pp. 756-763.
Supplementary European Search Report dated Jan. 30, 2018, regarding EP 15 81 9318.5.
Hoos, A. et al.: "*Metastatic Growth Progression Caused by PSGL-1-Mediated Recruitment of Monocytes to Metastatic Sites*"; Cancer Research, vol. 74, No. 3, Feb. 1, 2014, pp. 695-704.
Tinoco, Roberto et al.: "*PSGL-1 Is an Immune Checkpoint Regulator that Promotes T Cell Exhaustion*"; Immunity, Cell Press, US, vol. 44, No. 5, May 17, 2016, pp. 1190-1203.
Tripodo, C. et al.: "*P-Selectin Glycoprotein Ligand-1 as a Potential Target for Humoral Immunotherapy of Multiple Myeloma (Supplementary Material)*"; Current Cancer Drug Targets, vol. 9, No. 5, Aug. 2009, pp. 617-625.
Umeki, Saori et al.: "*Characterization of monoclonal antibodies against canine P-selectin glycoprotein ligand-1 (PSGL-1)*"; Veterinary Immunology & Immunopathology, vol. 142, No. 1, Apr. 13, 2011, pp. 119-125.
Yamaoka, Toshifumi et al.: "*The roles of P- and E-selectins and P-selectin glycoprotein ligand-1 in primary and metastatic mouse melanomas*"; J. of Dermatological Science, vol. 64, No. 2, Jul. 26, 2011, pp. 99-107.
Austin et al., "The Majority of Epidermal T Cells in Psoriasis Vulgaris Lesions can Produce Type 1 Cytokines, Interferon-γ, Interleukin-2, and Tumor Necrosis Factor-α, Defining TC1 (Cytotoxic T Lymphocyte) and TH1 Effector Populations: a Type 1 Differentiation Bias is also Measured in Circulating Blood T Cells in Psoriatic Patients," *J. Invest. Dermatol.* (1999), 113(5):752-759, The Society for Investigative Dermatology, Inc.

(Continued)

*Primary Examiner* — Rodney P Swartz

(74) *Attorney, Agent, or Firm* — Wilson Sonsini Goodrich & Rosati

(57) ABSTRACT

The present invention relates to the seminal discovery that P-selectin glycoprotein ligand-1 (PSGL-1) modulates the immune system and immune responses. Specifically, the present invention provides PSGL-1 agonists and antagonists which increase the survival of multifunctional T cells and viral clearance. The present invention further provides methods of treating infectious diseases, cancer and immune and inflammatory diseases and disorders using a PSGL-1 modulator.

8 Claims, 25 Drawing Sheets

(56) References Cited

OTHER PUBLICATIONS

Lord et al., "T-Bet is Required for Optimal Proinflammatory CD4+ T-Cell Trafficking," *Blood* (2005), 106(10):3432-3439, The American Society of Hematology.

Nishimura et al., "Human P-Selectin Glycoprotein Ligand-1 is a Functional Receptor for Enterovirus 71," *Nature Med.* (2009), 15(7):794-798, Nature America, Inc.

Swers et al., "A High Affinity Human Antibody Antagonist of P-Selectin Mediated Rolling," *Biochem. Biophys. Res. Comm.* (2006), 350:508-513, Elsevier Inc.

Urzainqui et al., "Functional Role of P-Selectin Glycoprotein Ligand 1/P-Selectin Interaction in the Generation of Tolerogenic Dendritic Cells," *J. Immunol.* (2007) 179:7457-7465, The American Association of Immunologists, Inc.

Huang et al. A novel apoptosis-inducing anti-PSGL-1 antibody for T cell-mediated diseases. Eur J Immuonl 35:2239-2249 (2005).

Nishimura. Infection mechanism of enterovirus 71. Uirusu 62(1):121-128 (2012) (English Abstract).

Raes et al. The metastatic T-cell hybridoma antigen/P-selectin glycoprotein ligand 1 is required for hematogenous metastasis of lymphomas. Int J Cancer 121:2646-2652 (2007).

Aubert et al. Antigen-specific CD4 T-cell help rescues exhausted CD8 T cells during chronic viral infection. PNAS USA 108(52):21182-21187 (2011).

Veerman et al. PSGL-1 regulates the migration and proliferation of CD8(+) T cells under homeostatic conditions. J Immunol 188(4):1638-1646 (2012).

Chunfeng et al. Preliminary study on the effect and mechanism of PSGL-1 crosslinking on aLβ2 integrin-mediated leukocyte adhesion. China Excellent Master Degree Thesis Full-text Database: Medical Science and Technology Series 4:L756-L763 (2014) (English Abstract).

\* cited by examiner

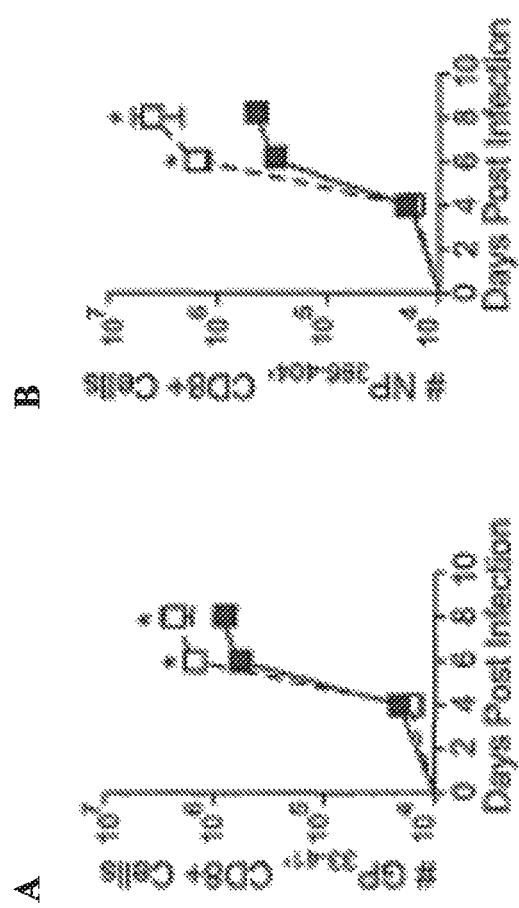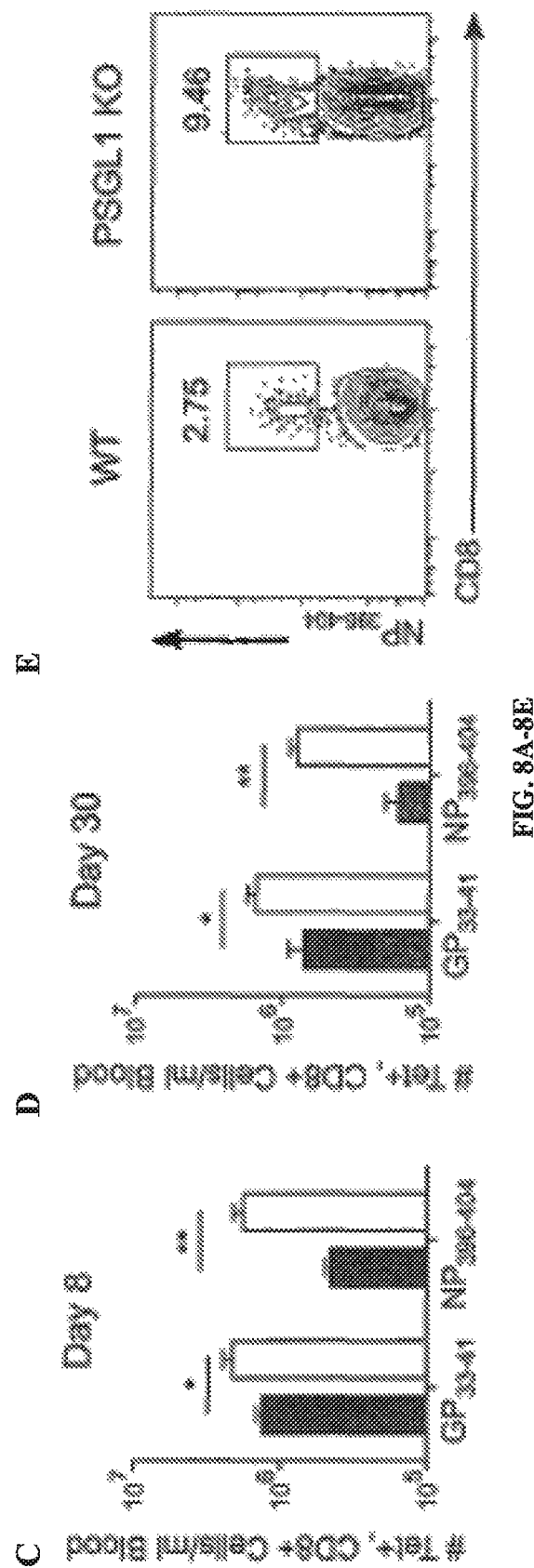
FIG. 8A-8E

PSGL-1 MODULATORS AND USES THEREOF

CROSS-REFERENCE TO RELATED APPLICATIONS

This application is a 35 USC § 371 National Stage application of International Application No. PCT/US2015/039586 filed Jul. 8, 2015; which claims the benefit under 35 USC § 119(e) to U.S. Application Ser. No. 62/022,191 filed Jul. 8, 2014. The disclosure of each of the prior applications is considered part of and is incorporated by reference in the disclosure of this application.

This invention was made with government support under P01 AI046530, R01 AI106895 and P30 CA030199 awarded by the National Institutes of Health. The United States government has certain rights in the invention.

FIELD OF THE INVENTION

The present invention relates to generally to antibodies and more specifically to the use of P-selectin glycoprotein ligand-1 (PSGL-1) modulators and uses thereof to modulate an immune response and treat infectious diseases, cancer and immune and inflammatory related diseases and disorders.

BACKGROUND OF THE INVENTION

Immune responses by T lymphocytes are critical for host protection against microbes, but they can become dysfunctional in chronic infections. With chronic viral infections, such as HIV and hepatitis B and C, T cell responses have a progressive loss of function and many T cells undergo apoptosis. The remaining T cells are arrested in a dysfunctional state, i.e. phenotypic exhaustion. Although is incompletely understood, several underlying mechanisms have been identified for T cell exhaustion in the lymphocytic chodomeningitits virus (LCMV) model of chronic infection with the Clone 13 strain (Cl13). In this model, virus-specific CD8+ T cells are chronically exposed to antigen and type I interferon resulting in an upregulated expression if immune inhibitory receptors including PD-1, LAG-3, CD160, and BTLA. The cells also lose motility, show altered transcriptional regulation, and have an increased production of the inhibitory cytokines, IL-10 and TGFβ. With time CD8+ T cells lose their proliferative potential, cytotoxic function and ability to produce IL-2, TNF-α and IFN-γ. CD4+ T cells display similarly altered differentiation with upregulation of inhibitory receptors and loss of function. Importantly, virus-specific CD4+ T cells can rescue exhausted CD8+ T cells, enabling them to mediate viral clearance. The production of IL-2 and IL-21 by CD4+ T cells is thought to contribute to reversal of the defective CD8+ T cell response-implying that key cytokines necessary for appropriate effector differentiation become limiting after chronic infection. Therefore an interplay of several integrated processes combine to disable the immune system's ability to eliminate chronic viral infections.

Many cancers including skin, lung, and kidney establish similar states of immune suppression and share many common features of immune dysfunction as those observed in chronic viral infections including HIV, Hepatitis B and C. These include death of responding T cells, and upregulation of inhibitory receptors including PD-1, Lag-3 and CTLA-4. As such, immunotherapies directed at boosting the critical functions of anti-tumor T cell responses are necessary to eradicate cancer in these settings. It is now evident that chronic viruses and tumors usurp the immune system by commandeering natural checks that prevent excessive immune responses. A major biomedical research problem is how to develop therapies to reverse this immunosuppression and promote tumor elimination.

It is now evident that reversing T cell dysfunction could reestablish immune responses and achieve disease resolution in a broad range of clinical settings. Adhesion mechanisms regulate the accumulation of T cells in both lymphoid and nonlymphoid tissues. Modulating adhesion molecule expression has been used to influence effector and memory T cell development and distinguish cells at different stages of differentiation. P-selectin glycoprotein ligand-1 (PSGL-1), a ligand for the selectin family of receptors, L, E, and P, is highly induced on T cells after chronic LCMV infection. PSGL-1 is primarily recognized for regulating T cell trafficking into inflamed tissues, and mediating T cell migration into lymphoid tissues under steady state conditions and after inflammatory responses. PSGL-1 can also regulate memory T cell homing to the bone marrow after a response resolves.

Despite new treatments that can greatly improve immune destruction of a broad range of cancers by blocking immune inhibitory receptors (e.g. PD-1/PD-L1, CTLA-4) and by anti-tumor T cells, efficacy is limited to subset of patients (often <30%). Thus, there is a critical need to develop new strategies to harness the immune system to achieve effective immunotherapy in the nonresponsive patients.

SUMMARY OF THE INVENTION

The present invention relates to the seminal discovery that P-selectin glycoprotein ligand-1 (PSGL-1) modulates the immune system and immune responses. Specifically, the present invention provides PSGL-1 agonists and antagonists which increase the survival of multifunctional T cells and viral clearance. The present invention further provides methods of treating infectious diseases, cancer and immune and inflammatory diseases and disorders using a PSGL-1 modulator.

In one embodiment, the present invention provides a method of treating a T cell mediated disease or disorder comprising administering a P-selectin glycoprotein ligand-1 (PSGL-1) modulator to a subject in need thereof. In one aspect, the PSGL-1 modulator is an agonist or antagonist. In another aspect, the T cell mediated disease or disorder is an infectious disease, cancer, an autoimmune disorder or an inflammatory disorder. In a specific aspect, the PSGL-1 modulator is an agonist and the T cell mediated disease or disorder is an autoimmune or inflammatory disease or disorder. In certain aspects, the PSGL-1 modulator is an antagonist and the T cell mediated disease or disorder is cancer or an infectious disease.

In one aspect, the PSGL-1 modulator is an antibody, a small molecule, a protein, a fusion protein or a nucleic acid. In a specific aspect, the antibody is a monoclonal antibody, chimeric antibody, human antibody or humanized antibody. In another aspect, CD4+ dependent CD8+ T cell response is increased. In an additional aspect, virus specific T cells are increased. In another aspect, Treg and DC response is increased. In a further aspect, expression of FoxP3, IL-10, TGF-β and/or MHC class II is increased. In an aspect, CD8+ secretion of IFNγ, TNFα and CD107 is increased. In other aspects, expression of PD-1, BTLA and CD160 is decreased or increased. In one aspect, expression of CD25 and T-bet is increased. In another aspect, viral clearance is increased.

In an additional embodiment, the present invention provides for a method of eliciting a T cell response comprising administering a PSGL-1 modulator to a subject in need thereof. In an aspect, the PSGL-1 modulator is an agonist or antagonist. In another aspect, the T cell mediated disease or disorder is an infectious disease, cancer, an autoimmune disorder or an inflammatory disorder. In one aspect, the PSGL-1 modulator is an antibody, a small molecule, a protein, a fusion protein or a nucleic acid. In a specific aspect, the antibody is a monoclonal antibody, chimeric antibody, human antibody or humanized antibody. In another aspect, CD4+ dependent CD8+ T cell response is increased. In an additional aspect, virus specific T cells are increased. In another aspect, Treg and DC response is increased. In a further aspect, expression of FoxP3, IL-10, TGF-β and/or MHC class II is increased. In an aspect, CD8+ secretion of IFNγ, TNFα and CD107 is increased. In other aspects, expression of PD-1, BTLA and CD160 is decreased or increased. In one aspect, expression of CD25 and T-bet is increased.

In a further embodiment, the present invention provides a method of restoring T cell function comprising administering a P-selectin glycoprotein ligand-1 (PSGL-1) modulator to a subject in need thereof. In an aspect, the PSGL-1 modulator is an agonist or antagonist. In another aspect, the T cell mediated disease or disorder is an infectious disease, cancer, an autoimmune disorder or an inflammatory disorder. In one aspect, the PSGL-1 modulator is an antibody, a small molecule, a protein, a fusion protein or a nucleic acid. In a specific aspect, the antibody is a monoclonal antibody, chimeric antibody, human antibody or humanized antibody. In another aspect, CD4+ dependent CD8+ T cell response is increased. In an additional aspect, virus specific T cells are increased. In another aspect, Treg and DC response is increased. In a further aspect, expression of FoxP3, IL-10, TGF-β and/or MHC class II is increased. In an aspect, CD8+ secretion of IFNγ, TNFα and CD107 is increased. In other aspects, expression of PD-1, BTLA and CD160 is decreased or increased. In one aspect, expression of CD25 and T-bet is increased.

In one embodiment, the present invention provides a pharmaceutical composition comprising a P-selectin glycoprotein ligand-1 (PSGL-1) modulator and a pharmaceutical carrier. In one aspect, the PSGL-1 modulator is an antibody, a small molecule, a protein, a fusion protein or a nucleic acid. In an additional aspect, the antibody is a monoclonal antibody, chimeric antibody, human antibody or humanized antibody.

BRIEF DESCRIPTION OF THE DRAWINGS

FIGS. 8A-E show the kinetics of virus-specific $CD8^+$ T cell response after Cl13 infection. WT (black squares or bars) or PSGL1-KO (white squares or bars) mice. (A-D) absolute number of $GP_{33-41}$+ or $NP_{396-404}$+ CD8+ T cells at day 4, 6, and 8 dpi (A,B, C) and 30 dpi (D). (E) dot plots represent a representative mouse.

DETAILED DESCRIPTION OF THE INVENTION

Figures 1A, 1B, 1C, 1D, 1E:
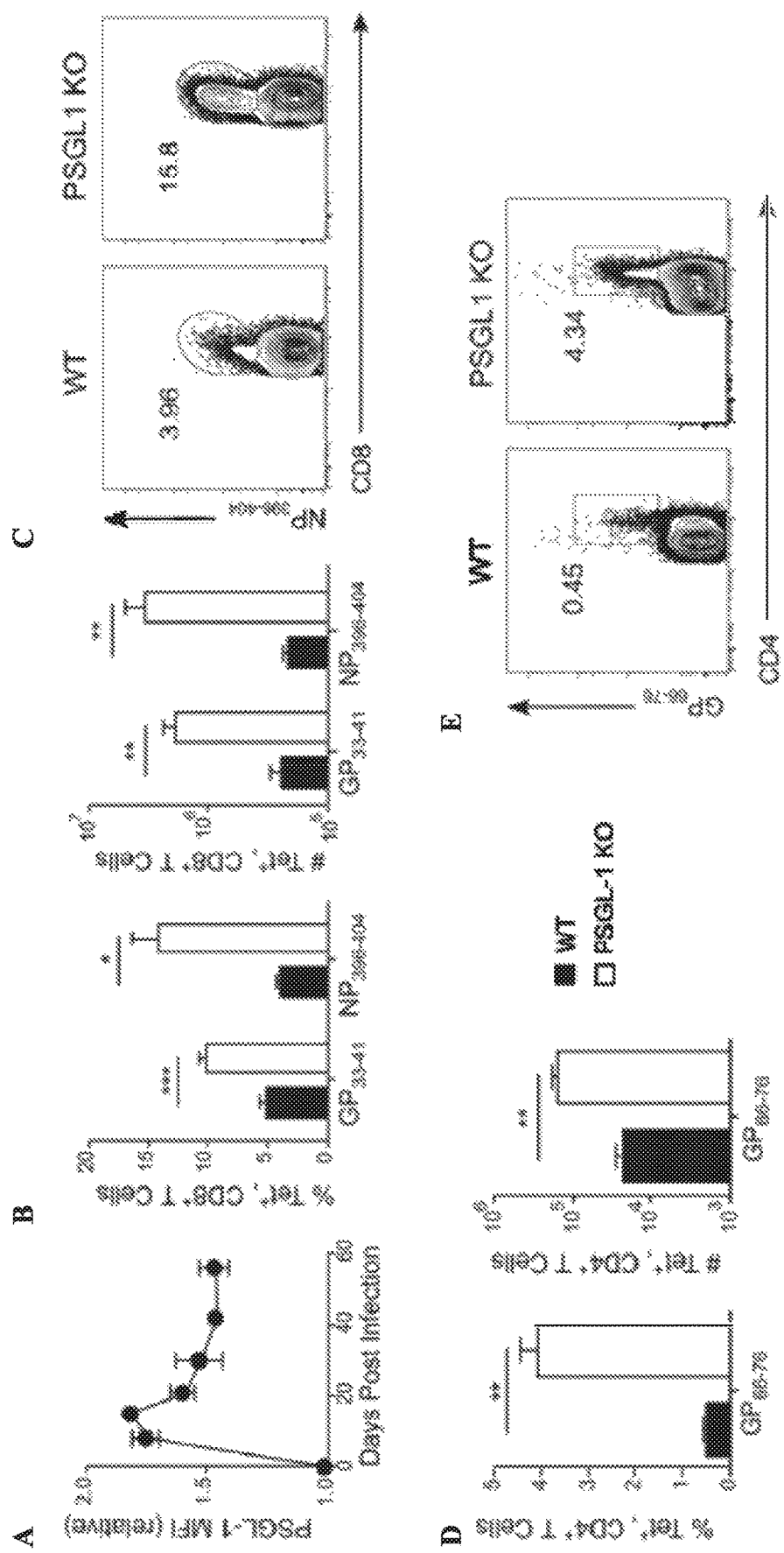
FIGS. 1A-E show PSGL-1 kinetics and accumulation of virus-specific T cells in PSGL-1 KO mice after LCMV Clone 13 infection. WT mice are represented by black bars or black circles and PSGL-1 KO mice are represented by white bars. (A) Mean fluorescence intensity (MFI) of PSGL-1 levels on $GP_{33-41}$+CD8+ T cells relative to CD8+ T cells in blood from uninfected WT mice. (B) Virus-specific CD8+ T cell frequencies and absolute numbers were enumerated in spleen at 8-days post infection (dpi). (C) FACS plots of virus-specific CD8+ T cell frequencies on $GP_{33-41}$+ CD8+ T cells. (D) Frequencies and absolute numbers of virus-specific $GP_{66-76}$+CD4+ T cells in spleen 8-dpi (E) FACS plots of virus-specific CD8+ T cell frequencies on virus-specific $GP_{66-76}$+CD4+ T cells.

The present invention relates to the seminal discovery that P-selectin glycoprotein ligand-1 (PSGL-1) modulates the immune system and immune responses. Specifically, the present invention provides PSGL-1 agonists and antagonists which increase the survival of multifunctional T cells and viral clearance. The present invention further provides methods of treating infectious diseases, cancer and immune and inflammatory diseases and disorders using a PSGL-1 modulator.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The definitions set forth below are for understanding of the disclosure but shall in no way be considered to supplant the understanding of the terms held by those of ordinary skill in the art.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. Each variable region is comprised of three segments called complementarity-determining regions (CDRs) or hypervariable regions and a more highly conserved portions of variable domains are called the framework region (FR). The variable domains of heavy and light chains each comprise four FR regions, largely adopting a β-sheet configuration, connected by three CDRs, which form loops connecting, and in some cases forming part of the β-sheet structure. The CDRs in each chain are held together in close proximity by the FRs and, with the CDRs from the other chain, contribute to the formation of the antigen-binding site of antibodies. The constant domains are not involved directly in binding an antibody to an antigen, but exhibit various effector functions, such as participation of the antibody in antibody dependent cellular cytotoxicity.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The Fc region of an antibody is the tail region of an antibody that interacts with cell surface receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains (CH domains 2-4) in each polypeptide chain. The Fc regions of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues.

The term "antibody" as used herein refers to intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably the antigen binding or variable region of the intact antibody. Examples of antibody fragments include Fab, Fab', F(ab')$_2$, and Fv fragments; diabodies, tribodies and the like; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore each monoclonal antibody is directed against a single determinant on the antigen. In addition to their specificity, the monoclonal antibodies are advantageous in that they are synthesized by the hybridoma culture, uncontaminated by other immunoglobulins. For example, the monoclonal antibodies to be used in accordance with the present invention may be made by hybridomas, by recombinant DNA methods or isolated from phage antibody libraries.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding.

The terms "fusion molecule" and "fusion protein" are used interchangeably and are meant to refer to a biologically active polypeptide usually a HVEM or antibody and an effector molecule usually a protein or peptide sequence covalently linked (i.e. fused) by recombinant, chemical or other suitable method. If desired, the fusion molecule can be fused at one or several sites through a peptide linker sequence. Alternatively, the peptide linker may be used to assist in construction of the fusion molecule. Specifically preferred fusion molecules are fusion proteins. Generally fusion molecule also can be comprised of conjugate molecules.

Fc-Fusion proteins (also known as Fc chimeric fusion protein, Fc-Ig, Ig-based Chimeric Fusion protein and Fc-tag protein) are composed of the Fc domain of IgG genetically linked to a peptide or protein of interest. Fc-Fusion proteins have become valuable reagents for in vivo and in vitro research.

The Fc-fused binding partner can range from a single peptide, a ligand that activates upon binding with a cell surface receptor, signaling molecules, the extracellular domain of a receptor that is activated upon dimerization or as a bait protein that is used to identify binding partners in a protein microarray.

One of the most valuable features of the Fc domain in vivo, is it can dramatically prolong the plasma half-life of the protein of interest, which for bio-therapeutic drugs, results in an improved therapeutic efficacy; an attribute that has made Fc-Fusion proteins attractive bio-therapeutic agents.

As used herein, the terms "nucleic acids" or "nucleic acid sequences" refer to oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., e.g., double stranded iRNAs, e.g., iRNPs), nucleic acids, i.e., oligonucleotides, containing known analogues of natural nucleotides.

As used herein, the terms "polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition. In various embodiments the polypeptides can have at least 10 amino acids or at least 25, or at least 50 or at least 75 or at least 100 or at least 125 or at least 150 or at least 175 or at least 200 amino acids.

As used herein, the term "small molecule" refers to a low molecular weight (<900 daltons) organic compound that may help regulate a biological process, with a size on the order of $10^{-9}$ m. Most drugs are small molecules. Small molecules can have a variety of biological functions, serving as cell signaling molecules, as drugs in medicine, as pesticides in farming, and in many other roles. These compounds can be natural (such as secondary metabolites) or artificial (such as antiviral drugs); they may have a beneficial effect against a disease (such as drugs) or may be detrimental (such as teratogens and carcinogens). Biopolymers such as nucleic acids and proteins, and polysaccharides (such as starch or cellulose) are not small molecules—though their constituent monomers-ribo- or deoxyribonucleotides, amino acids, and monosaccharides, respectively-are often considered small molecules.

As used herein, the terms "treating" or "treatment" or "alleviation" refer to therapeutic treatment, prophylactic and/or preventative measures, wherein the object is to prevent or slow down (lessen) the targeted pathologic condition or disorder. Those in need of treatment include those already with the disorder as well as those prone to have the disorder or those in whom the disorder is to be prevented.

The term "therapeutic agent" as used herein includes a chemical compound or composition capable of inducing a desired therapeutic effect when administered to a patient or subject. An example of a therapeutic agent of the present invention is an anti-PSGL-1 antibody or a PSGL-1 fusion protein.

As used herein, the terms "effective amount" or "therapeutically effective amount" of a drug used to treat a disease is an amount that can reduce the severity of a disease, reduce the severity of one or more symptoms associated with the disease or its treatment, or delay the onset of more serious symptoms or a more serious disease that can occur with some frequency following the treated condition. An "effective amount" may be determined empirically and in a routine manner, in relation to the stated purpose.

The therapeutic agent may be administered by any suitable means, including topical, parenteral, subcutaneous, intraperitoneal, intrapulmonary, intranasal, intravenous, and/or intralesional administration in order to treat the subject.

As used herein, the term "T cell mediated disease or disorder" refers to any condition that would benefit from treatment with a PSGL-1 modulator. Examples of diseases and disorders that would benefit from anti-PSGL-1 treatment include infectious diseases, cancer and immune, autoimmune and inflammatory diseases and disorders. In particular, subjects having cancer or an infectious disease can benefit from PSGL-1 antagonist treatment and subjects having an autoimmune or inflammatory disease or disorder can benefit from PSGL-1 agonist treatment.

An infection occurs when an organism's body is invaded by pathogenic viruses, infectious virus particles (virions), fungus or bacteria that can attach to and enter susceptible cells. A vast number of viruses cause infectious diseases. Examples of infectious diseases include, but are not limited to, Botulism, Bubonic plague, Calicivirus infection (Norovirus and Sapovirus), Chickenpox, *Chlamydia*, Cholera, *Clostridium difficile* infection, Common cold (Acute viral rhinopharyngitis; Acute coryza), Creutzfeldt-Jakob disease (CJD), Dengue fever, Diphtheria, Ebola hemorrhagic fever, Gonorrhea, Hand, foot and mouth disease (HFMD), *Helicobacter pylori* infection, Hepatitis A, Hepatitis B, Hepatitis C, Hepatitis D, Hepatitis E, Herpes simplex, human immunodeficiency virus (HIV), Human papillomavirus (HPV) infection, Epstein-Barr Virus Infectious Mononucleosis (Mono), Influenza (flu), Legionellosis (Legionnaires' disease), Leprosy, Lyme disease (Lyme borreliosis), Malaria, Marburg hemorrhagic fever (MHF), Measles, Middle East respiratory syndrome (MERS), Meningitis, Mumps, Pertussis (Whooping cough), Plague, Progressive multifocal leukoencephalopathy, Rabies, Rhinovirus infection, Rocky Mountain spotted fever (RMSF), Rubella, *Salmonellosis*, SARS (Severe Acute Respiratory Syndrome), Scabies, Sepsis, Shigellosis (Bacillary dysentery), Shingles (Herpes zoster), Smallpox (Variola), Syphilis, Tetanus (Lockjaw), Tuberculosis, Typhoid Fever, Valley fever, Viral pneumonia, West Nile Fever, and Yellow fever.

Infectious diseases are commonly treated with anti-viral agents, anti-bacterial agents or anti-fungal agents. Anti-viral agents included, but are not limited to, Abacavir, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir and Zidovudine.

Anti-bacterial agents include, but are not limited to, Amikacin, Gentamicin, Kanamycin, Neomycin, Netilmicin, Tobramycin, Paromomycin, Streptomycin, Spectinomycin (Bs), Geldanamycin, Herbimyci, Rifaximin, Loracarbef, Ertapenem, Doripenem, Imipenem/Cilastatin, Meropenem, Cefadroxil, Cefazolin, Cefalotin or Cefalothin), Cefalexin, Cefaclor, Cefprozil, Cefuroxime, Cefixime, Cefdinir, Cefditoren, Cefoperazone, Cefotaxime, Cefpodoxime, Ceftazidime, Ceftibuten, Ceftizoxime), Ceftriaxone, Cefepime, Ceftaroline fosamil, Ceftobiprole, Teicoplanin, Vancomycin, Telavancin, Dalbavancin, Oritavanci, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin(Bs), Oxazolidinones(Bs), Linezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin, Penicillin, Piperacillin, Penicillin G, Temocillin, Ticarcillin, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim, Demeclocycline, Doxycycline, Minocycline, Oxytetracycline, Tetracycline, Streptomycin and Fosfomycin.

Anti-fungal agents include, but are not limited to, Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Efinaconazole, Epoxiconazole, Fluconazole, Isavuconazole, Itraconazole, Posaconazole, Propiconazole, Ravuconazole, Terconazole, Voriconazole, Abafungin, Amorolfin, Butenafine, Naftifine, Terbinafine, Anidulafungin, Caspofungin, and Micafungin.

An immune disease or disorder is a dysfunction of the immune system. These disorders can be characterized in several different ways: by the component(s) of the immune system affected; by whether the immune system is overactive or underactive and by whether the condition is congenital or acquired. Autoimmune diseases arise from an abnormal immune response of the body against substances and tissues normally present in the body (autoimmunity). A major understanding of the underlying pathophysiology of autoimmune diseases has been the application of genome wide association scans that have identified a striking degree of genetic sharing among the autoimmune diseases.

Autoimmune disorders include, but are not limited to, Acute disseminated encephalomyelitis (ADEM), Addison's disease, Agammaglobulinemia, Alopecia areata, Amyotrophic lateral sclerosis (aka Lou Gehrig's disease), Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behcet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, graft versus host disease, Graves' disease, Guillain-Barré syndrome, Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease, Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka *Pityriasis* lichenoides et varioliformis *acuta*, Multiple sclerosis, Myasthenia gravis, Myositis, Meniere's disease, Narcolepsy, Neuromyelitis optica, Neuromyotonia, Ocular cicatricial pemphigoid, Opsoclonus myoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis *nodosa*, Polymyalgia rheumatica, Polymyositis, Primary biliary cirrhosis, Primary sclerosing cholangitis, Progressive inflammatory neuropathy, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome, Schnitzler syndrome, Scleritis, Scleroderma, Serum Sickness, Sjögren's syndrome, Spondyloarthropathy, Stiff person syndrome, Still's disease, Subacute bacterial endocarditis (SBE), Susac's syndrome, Sweet's syndrome, Sydenham chorea, Sympathetic ophthalmia, Systemic lupus erythematosus, Takayasu's arteritis, Temporal arteritis, Thrombocytopenia, Tolosa-Hunt syndrome, Transverse myelitis, Ulcerative colitis, Undifferentiated spondyloarthropathy, Urticarial vasculitis, Vasculitis, Vitiligo, Wegener's granulomatosis.

Inflammatory disease are a large group of disorders that underlie a vast variety of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease. A large variety of proteins are involved in inflammation, and any one of them is open to a genetic mutation which impairs or otherwise dysregulates the normal function and expression of that protein. Examples of disorders associated with inflammation include Acne vulgaris, Asthma, Autoimmune diseases, Celiac disease, Chronic prostatitis, Glomerulonephritis, Hypersensitivities, Inflammatory bowel diseases, Pelvic inflammatory disease, Reperfusion injury, Rheumatoid arthritis, Sarcoidosis, Transplant rejection, Vasculitis, Interstitial cystitis, Atherosclerosis, Allergies, Myopathies, leukocyte defects and cancer.

The term "immune modulator" as used herein refers to any therapeutic agent that modulates the immune system. Examples of immune modulators include eicosanoids, cytokines, prostaglandins, interleukins, chemokines, checkpoint regulators, TNF superfamily members, TNF receptor superfamily members and interferons. Specific examples of immune modulators include PGI2, PGE2, PGF2, CCL14, CCL19, CCL20, CCL21, CCL25, CCL27, CXCL12, CXCL13, CXCL-8, CCL2, CCL3, CCL4, CCL5, CCL11, CXCL10, IL1, IL2, IL3, IL4, IL5, IL6, IL7, IL8, IL9, IL10, IL11, IL12, IL13, IL15, IL17, IL17, INF-α, INF-β, INF-ε, INF-γ, G-CSF, TNF-α, CTLA, CD20, PD1, PD1L1, PD1L2, ICOS, CD200, CD52, LTα, LTαβ, LIGHT, CD27L, 41BBL, FasL, Ox40L, April, TL1A, CD30L, TRAIL, RANKL, BAFF, TWEAK, CD40L, EDA1, EDA2, APP, NGF, TNFR1, TNFR2, LTβR, HVEM, CD27, 4-1BB, Fas, Ox40, AITR, DR3, CD30, TRAIL-R1, TRAIL-R2, TRAIL-R3, TRAIL-R4, RANK, BAFFR, TACI, BCMA, Fn14, CD40, EDAR XEDAR, DR6, DcR3, NGFR-p75, and Taj. Other examples of immune modulators include tocilizumab (Actemra), CDP870 (Cimzia), enteracept (Enbrel), adalimumab (Humira), Kineret, abatacept (Orencia), infliximab (Remicade), rituzimab (Rituxan), golimumab (Simponi), Avonex, Rebif, ReciGen, Plegridy, Betaseron, Copaxone, Novatrone, natalizumab (Tysabri), fingolimod (Gilenya), teriflunomide (Aubagio), BG12, Tecfidera, and alemtuzumab (Campath, Lemtrada).

Cancer is a group of diseases involving abnormal cell growth with the potential to invade or spread to other parts of the body. Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS—Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood'; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

The term "chemotherapeutic agent" as used herein refers to any therapeutic agent used to treat cancer. Examples of chemotherapeutic agents include, but are not limited to, Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (dacliximab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, and natalizumab.

The immune system is a system of biological structures and processes within an organism that protects against disease. This system is a diffuse, complex network of interacting cells, cell products, and cell-forming tissues that protects the body from pathogens and other foreign substances, destroys infected and malignant cells, and removes cellular debris: the system includes the thymus, spleen, lymph nodes and lymph tissue, stem cells, white blood cells, antibodies, and lymphokines. B cells or B lymphocytes are a type of lymphocyte in the humoral immunity of the adaptive immune system and are important for immune surveillance. T cells or T lymphocytes are a type of lymphocyte that plays a central role in cell-mediated immunity. There are two major subtypes of T cells: the killer T cell and the helper T cell. In addition there are suppressor T cells which have a role in modulating immune response. Killer T cells only recognize antigens coupled to Class I MHC molecules, while helper T cells only recognize antigens coupled to Class II MHC molecules. These two mechanisms of antigen presentation reflect the different roles of the two types of T cell. A third, minor subtype are the γδ T cells that recognize intact antigens that are not bound to MHC receptors. In contrast, the B cell antigen-specific receptor is an antibody molecule on the B cell surface, and recognizes whole pathogens without any need for antigen processing. Each lineage of B cell expresses a different antibody, so the complete set of B cell antigen receptors represent all the antibodies that the body can manufacture.

P-selectin glycoprotein ligand-1 (PSGL-1) is expressed by hematopoietic cells, and is a highly conserved ligand for the selectin family of adhesion molecules, P, E, and L, known for initiating cell migration. Selectins are part of the broader family of cell adhesion molecules. PSGL-1 can bind to all three members of the family but binds with the highest affinity to P-selectin. PSGL-1, a heavily glycosylated sialomucin expressed on most leukocytes, has dual function as a selectin ligand for leukocyte rolling on vascular selectins expressed in inflammation and as a facilitator of resting T cell homing into lymphoid organs. PSGL-1 has been found to play a role in other contexts such as hematopoietic stem cell homing to the bone marrow, progenitor homing to thymus, and T cell homing to SLOs through interactions with chemokines. PSGL-1 deficiency appears to influence CD8+ T cell homeostasis in at least three different ways: 1) by interfering with lymph node entry of T cells, thereby limiting access to homeostatic cytokines and other prosurvival signals in the lymph node; 2) by prolonging lymph node residence time, thereby extending exposure of T cells to prosurvival signals therein; and 3) by increasing T cell sensitivity to cytokines.

Chronic viral infections represent an altered state of homeostasis, an intricate balance between host and pathogen where both survive, albeit at the expense of suppression of the host immune system. Although the adhesion molecule PSGL-1 is thought to function primarily in cell migration, its expression, signaling capacity, and binding specificity suggest additional roles during infection.

PSGL-1 is a previously unrecognized negative regulator of T cell responses that is linked to expression levels of multiple immune inhibitory receptors. Therefore, PSGL-1 has significant translational potential for treating immune and inflammatory disorders, including cancer. It has been shown that PSGL-1 deficiency enables CD8+ T cells to mount greater effector responses to influenza and lymphocytic choriomenengitis (LCMV) viruses in murine models, as measured by enhanced cytotoxicity, cytokine production, and viral clearance. Moreover, effector and memory T cells persist in elevated frequencies due to improved survival. In a chronic infection model with the LCMV-variant strain, Clone 13, PSGL-1-deficiency prevents chronic infection. CD8+ T cells retain effector functions and fail to develop the hallmarks of exhaustion that include high expression of PD-1 as well several other inhibitory receptors. CD8+ T cells with characteristics of exhaustion are found in the blood, lymph nodes, and tumor-infiltrating cells of melanoma patients. Although clinical trials with anti-PD-L1, -PD-1, or -CTLA-4 have shown some remarkable efficacy, the concept that blocking multiple receptors will have greater impact is suggested by studies of T cells from melanoma patients. Since greater function of PSGL-1 KO T cells is associated with lower levels of multiple inhibitory receptors, we propose that blocking PSGL-1 could have the necessary attributes to improve T cell immune responses to melanoma. PSGL-1 is also expressed by regulatory T cells (Tregs) and DCs, whose tolerogenic functions are lost with PSGL-1 deficiency. Thus, blocking PSGL-1 could not only enhance the responses of effector T cells but also limit the immunosuppressive responses of Tregs and DCs.

As described in the examples below, it was established that PSGL-1 unexpectedly plays a role as a regulator of T cell function that can be exploited by a chronic virus to keep effector T cell immunity in check thus permitting a persistent infection but also limiting immune mediated host tissue damage. In PSGL-1-deficient hosts, the CD8+ and CD4+ T cells failed to acquire hallmarks of T cell exhaustion, and instead developed into robust multifunctional effectors that were maintained at elevated levels and together promoted early viral clearance, outcomes that mechanistically required CD4+ T cells. This effective anti-viral immunity was linked to reduced expression of inhibitory receptors on both CD8+ and CD4+ T cells, as well as increased systemic levels of proinflammatory cytokines and immune pathology. In the absence of CD4+ T cells, the CD8+ T cells in PSGL-1-deficient mice failed to down regulate inhibitory receptors, displayed functional exhaustion, and were unable to support viral clearance. Therefore, relieving PSGL-1-dependent inhibition of CD4+ cells is key to inducing an effective anti-viral response by CD8+ T cells. PSGL-1 also plays a T cell intrinsic role in limiting CD8+ and CD4+ effector cell survival, that could also contribute to reduced viral control.

Persistent viral replication following Cl13 infection drives CD8+ T cell exhaustion and apoptosis by extinguishing production, availability, and responses to the γc survival cytokines, IL-2, IL-7, and IL-21. Importantly, PSGL-1-deficiency was associated with increased and sustained expression of IL-7Rα as well as Bcl-2, suggesting that enhanced IL-7Rα signaling provides one mechanism to improve effector T cell survival. This conclusion is supported by the finding that therapeutic administration of IL-7 expands virus-specific CD8+ T cells, increases their effector function, and prevents persisting Cl13 infection. The increased expression of the high affinity IL-2 receptor, CD25, on PSGL-1-deficient CD8+ T cells, and greater availability of IL-2 from CD4+ T cells could also underlie improved CD8+ as well as CD4+ T cell survival and function. Previous studies showed that IL-2 increases virus-specific CD8+ T cells and reduces viral loads when administered to Cl13 infected mice. Since the progressive loss of function by CD8+ T cells can lead to elimination of high affinity clones by apoptosis mediated by TGF-α that can be reversed by IL-2 and IL-7, our findings suggest that in combination, enhanced IL-7 and IL-2 signals to virus-specific CD8−+ T cells could contribute to the mechanisms of survival. However, since elevated serum levels of IL-21 were detected at the peak of the CD8+ T cell response in PSGL-1-deficient mice and IL-21 sustains virus-specific CD8+ T cells during chronic LCMV infection, this γc cytokine that is produced by CD4+ T cells as well as other cell types could also contribute to the mechanism of virus-specific CD8+ T cell survival. It was also observed increased levels of IL-6, which is necessary for the generation and function of T follicular helper cells (Tfh), thereby leading to improved antibody responses that contribute to ultimate control of chronic LCMV. The results described below indicate that in WT mice, PSGL-1 plays a central role in dampening the T cell response to Cl13 by limiting virus-specific CD8+ and CD4+ T cell survival responses to several pro-survival cytokines and by constraining production of key cytokines implicated in CD4 T cell help.

Chronic viral infections maintain anti-viral T cell responses in a state of dysfunction that is associated with several immune inhibitory receptors. It is striking that each of the receptors analyzed, PD-1, CD160 and BTLA, was down-modulated on PSGL-1-deficient CD8+ and CD4+ effectors after Cl13 infection and the anti-viral response was dramatically improved. The results imply that PSGL-1 is normally a key part of a regulatory program that prevents excessive T cell responses. PSGL-1-deficiency had no apparent effect on resting T cells nor did it lead to inherent inflammatory responses; however, its absence results in immunopathology and increased mortality after Cl13 infection. This underscores the function of PSGL-1 in balancing excessive T cell responses and host tissue destruction to persistent antigen. Mechanistically, it was found that ligating PSGL-1 during antigen stimulation led to reduced survival of exhausted CD8+ T cells and upregulated PD-1 on the remaining viable cells, indicating that PSGL-1 signaling links to expression of this receptor.

Changes in transcriptional regulation that are usually associated with CD8+ T cell dysfunction include reduced expression of homes and enhanced T-bet, which favor effector differentiation during chronic infection as opposed to memory formation during acute infection. These transcription factors have opposing roles in chronic LCMV infection with more exhausted virus-specific CD8+ T cells expressing higher levels of homes and reduced T-bet levels. Since elevated T-bet expression represses PD-1 expression, it is striking that PSGL-1 deficiency caused reduced homes and more T-bet, further supporting the concept that changes in transcriptional regulation and markers of exhaustion are linked to PSGL-1 expression.

High PSGL-1 expression can be found on many cells types, including DCs and Tregs where it has been associated with functional regulation, delineating tolerogenic DCs and the most suppressive Tregs. Therefore, PSGL-1 could play roles on other cells that indirectly contribute to T cell dysfunction during chronic infection. However, our results indicate that these effects, if occurring in the context of PSGL-1-deficiency, require the activity of CD4$^+$ T cells to realize the regulatory activity of PSGL-1. PSGL-1-deficient mice have been reported to have a subtle phenotype and our data indicate that infection is necessary to induce the profound PSGL-1-dependent inhibitory effects. Despite altered trafficking of pre-T cells to the thymus, and of naive CD4$^+$ T cells to lymph nodes peripheral naive T cells appear to be generated normally in the absence of PSGL-1, although memory phenotype cells are somewhat increased possibly due to greater turnover. Given the T cell intrinsic effects of PSGL-1-deficiency on effector cell survival and the reversal of the enhanced anti-viral immunity with CD4$^+$ T cell depletion, more subtle aspects of regulation in the context of PSGL-1 deficiency do not appear to make a substantive contribution to the outcomes of this study.

Recent clinical trials with anti-PD-1/PD-L1 and/or CTLA-4 support the concept that immunity to chronic virus or tumors can be improved by interfering with inhibitory pathways. Furthermore, targeting combinations of inhibitory receptors can lead to greater efficacy and since multiple inhibitory receptors are decreased by PSGL-1, this receptor could be a novel target whose inhibition might improve T cell responses in several clinical contexts.

In one embodiment, the present invention provides a method of treating a T cell mediated disease or disorder comprising administering a P-selectin glycoprotein ligand-1 (PSGL-1) modulator to a subject in need thereof. In one aspect, the PSGL-1 modulator is an agonist or antagonist. In another aspect, the T cell mediated disease or disorder is an infectious disease, cancer, an autoimmune disorder or an inflammatory disorder. In an additional aspect, the infectious disease is Botulism, Bubonic plague, Calicivirus infection (Norovirus and Sapovirus), Chickenpox, *Chlamydia*, Cholera, *Clostridium difficile* infection, Common cold (Acute viral rhinopharyngitis; Acute coryza), Creutzfeldt-Jakob disease (CJD), Dengue fever, Diphtheria, Ebola hemorrhagic fever, Gonorrhea, Hand, foot and mouth disease (HFMD), *Helicobacter pylori* infection, Hepatitis A, Hepatitis B, Hepatitis C, Hepatitis D, Hepatitis E, Herpes simplex, human immunodeficiency virus (HIV), Human papillomavirus (HPV) infection, Epstein-Barr Virus Infectious Mononucleosis (Mono), Influenza (flu), Legionellosis (Legionnaires' disease), Leprosy, Lyme disease (Lyme borreliosis), Malaria, Marburg hemorrhagic fever (MHF), Measles, Middle East respiratory syndrome (MERS), Meningitis, Mumps, Pertussis (Whooping cough), Plague, Progressive multifocal leukoencephalopathy, Rabies, Rhinovirus infection, Rocky Mountain spotted fever (RMSF), Rubella, *Salmonellosis*, SARS (Severe Acute Respiratory Syndrome), Scabies, Sepsis, Shigellosis (Bacillary dysentery), Shingles (Herpes zoster), Smallpox (Variola), Syphilis, Tetanus (Lockjaw), Tuberculosis, Typhoid Fever, Valley fever, Viral pneumonia, West Nile Fever, or Yellow fever. In certain aspect, the cancer is prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract. In a further aspect, the autoimmune disorder is Addison's disease, amyotrophic lateral sclerosis, Crohn's disease, Cushing's Syndrome, diabetes mellitus type 1, graft versus host disease, Graves' disease, Guillain-Barré syndrome, lupus erythematosus, multiple sclerosis, psoriasis, psoriatic arthritis, rheumatoid arthritis, sarcoidosis, scleroderma, systemic lupus erythematosus, transplant rejection, or vasculitis. In a specific aspect, the PSGL-1 modulator is an agonist and the T cell mediated disease or disorder is an autoimmune or inflammatory disease or disorder. In certain aspects, the PSGL-1 modulator is an antagonist and the T cell mediated disease or disorder is cancer or an infectious disease.

In one aspect, the PSGL-1 modulator is an antibody, a small molecule, a protein, a fusion protein or a nucleic acid. In a specific aspect, the antibody is a monoclonal antibody, chimeric antibody, human antibody or humanized antibody. In another aspect, CD4+ dependent CD8+ T cell response is increased. In an additional aspect, virus specific T cells are increased. In another aspect, Treg and DC response is increased. In a further aspect, expression of FoxP3, IL-10, TGF-β and/or MHC class II is increased. In an aspect, CD8+ secretion of IFNγ, TNFα and CD107 is increased. In other aspects, expression of PD-1, BTLA and CD160 is decreased or decreased. In one aspect, expression of CD25 and T-bet is increased. In another aspect, viral clearance is increased. In an additional aspect, the method further comprises the administration of a therapeutic agent. In a further aspect, the therapeutic agent is an immune modulator, a chemotherapeutic agent, an anti-viral agent, an anti-bacterial agent or an anti-fungal agent.

In an additional embodiment, the present invention provides for a method of eliciting a T cell response comprising administering a PSGL-1 modulator to a subject in need thereof. In an aspect, the PSGL-1 modulator is an agonist or antagonist. In another aspect, the T cell mediated disease or disorder is an infectious disease, cancer, an autoimmune disorder or an inflammatory disorder. In one aspect, the PSGL-1 modulator is an antibody, a small molecule, a protein, a fusion protein or a nucleic acid. In a specific aspect, the antibody is a monoclonal antibody, chimeric antibody, human antibody or humanized antibody. In another aspect, CD4+ dependent CD8+ T cell response is increased. In an additional aspect, virus specific T cells are increased. In another aspect, Treg and DC response is increased. In a further aspect, expression of FoxP3, IL-10, TGF-β and/or MHC class II is increased. In an aspect, CD8+ secretion of IFNγ, TNFα and CD107 is increased. In other aspects, expression of PD-1, BTLA and CD160 is decreased or increased. In one aspect, expression of CD25 and T-bet is increased.

In a further embodiment, the present invention provides a method of restoring T cell function comprising administering a P-selectin glycoprotein ligand-1 (PSGL-1) modulator to a subject in need thereof. In an aspect, the PSGL-1 modulator is an agonist or antagonist. In another aspect, the T cell mediated disease or disorder is an infectious disease, cancer, an autoimmune disorder or an inflammatory disorder. In one aspect, the PSGL-1 modulator is an antibody, a small molecule, a protein, a fusion protein or a nucleic acid. In a specific aspect, the antibody is a monoclonal antibody, chimeric antibody, human antibody or humanized antibody. In another aspect, CD4+ dependent CD8+ T cell response is increased. In an additional aspect, virus specific T cells are increased. In another aspect, Treg and DC response is increased. In a further aspect, expression of FoxP3, IL-10, TGF-β and/or MHC class II is increased. In an aspect, CD8+ secretion of IFNγ, TNFα and CD107 is increased. In other aspects, expression of PD-1, BTLA and CD160 is decreased or increased. In one aspect, expression of CD25 and T-bet is increased. In an additional aspect, the method further comprises the administration of a therapeutic agent. In a further aspect, the therapeutic agent is an immune modulator, a chemotherapeutic agent, an anti-viral agent, an anti-bacterial agent or an anti-fungal agent.

In one embodiment, the present invention provides a pharmaceutical composition comprising a P-selectin glycoprotein ligand-1 (PSGL-1) modulator and a pharmaceutical carrier. In one aspect, the PSGL-1 modulator is an antibody, a small molecule, a protein, a fusion protein or a nucleic acid. In an additional aspect, the antibody is a monoclonal antibody, chimeric antibody, human antibody or humanized antibody.

The invention in all its aspects is illustrated further in the following Examples. The Examples do not, however, limit the scope of the invention, which is defined by the appended claims.

EXAMPLES

Example 1

Figures 7A, 7B, 7C, 7D, 7E:
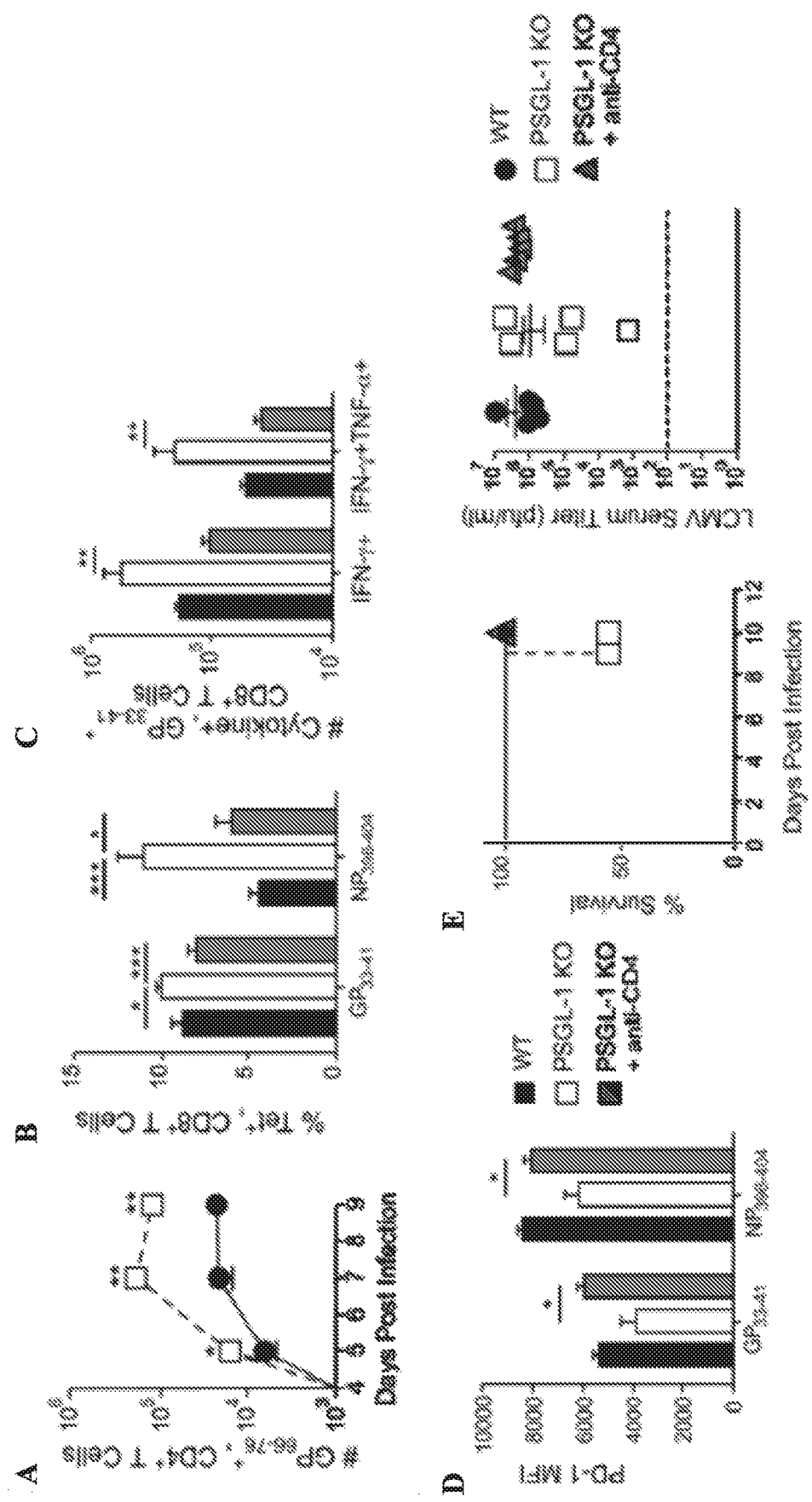
FIGS. 7A-E show that optimal virus-specific CD8+ T cell function in PSGL-1 KO mice depends on CD4+ T cell help. WT mice represented by black bars or black circles, PSGL-1 KO mice represented by white bars or white squares and PSGL-1 KO CD4-depleted mice represented by gray bars or gray triangles. (A) absolute numbers of $GP_{66-76}$+CD4+ T cells in spleen. (B) frequencies of $GP_{33-41}$ and $NP_{396-404}$ CD8+ T cells in blood at 8-dpi (C) absolute number of cytokine producing $GP_{33-41}$ CD8+ T cells in spleen at 10-dpi (D) PD-1 levels on $GP_{33-41}$+ and $NP_{396-404}$+ specific CD8+ T cells in spleen at day 10 dpi (E) survival and serum viral levels at 10-dpi.

PSGL-1 Expression is Increased on Virus-Specific CD8+ T Cells and PSGL-1 Deficient Mice have an Accumulation of Virus-Specific T Cells During Cl13 Infection To study PSGL-1 in chronic viral infection, the LCMV Cl13 virus was used which results in viremia to 90-dpi and detectable virus in brain and kidney to 200-days post infection (dpi). PSGL-I levels on CD8+ T cells specific for the $GP_{33-41}+$ LCMV epitope was first examined by tetramer staining. Although. PSGL-1 is expressed by all T cells, the levels were increased on virus-specific compared to naïve CD8+ T cells (FIG. 1a). To examine contributions of PSGL-1 to the anti-viral response, WT or PSGL-1-deficient mice were infected with Cl13 and analyzed CD8+ T cells specific for the LCMV $GP_{33-41}+$ and $NP_{396}$-404+ epitopes. PSGL-1-deficient mice had greatly increased frequencies and numbers of $GP_{33-41}+CD8+$ T cells at 8-dpi (FIG. 1b). The difference in CD8+ T cell accumulation was not observed until after 4-dpi (FIG. 8a-b) and tetramer cells were maintained through 30-dpi (FIG. 8c-e). Most impressive was the preservation of $NP_{396-404}+$ T cells in PSGL-1-deficient mice (FIG. 1b,c), as these cells are largely deleted by 30-dpi in WT mice (FIG. 8c-e). It was also found that virus-specific $GP_{66-76}+CD4+$ T cells were increased in PSGL-1-deficient mice (FIG. 1d,e). This difference was observed by 5-dpi (FIG. 7a).

Figures 9A, 9B, 9C, 9D:
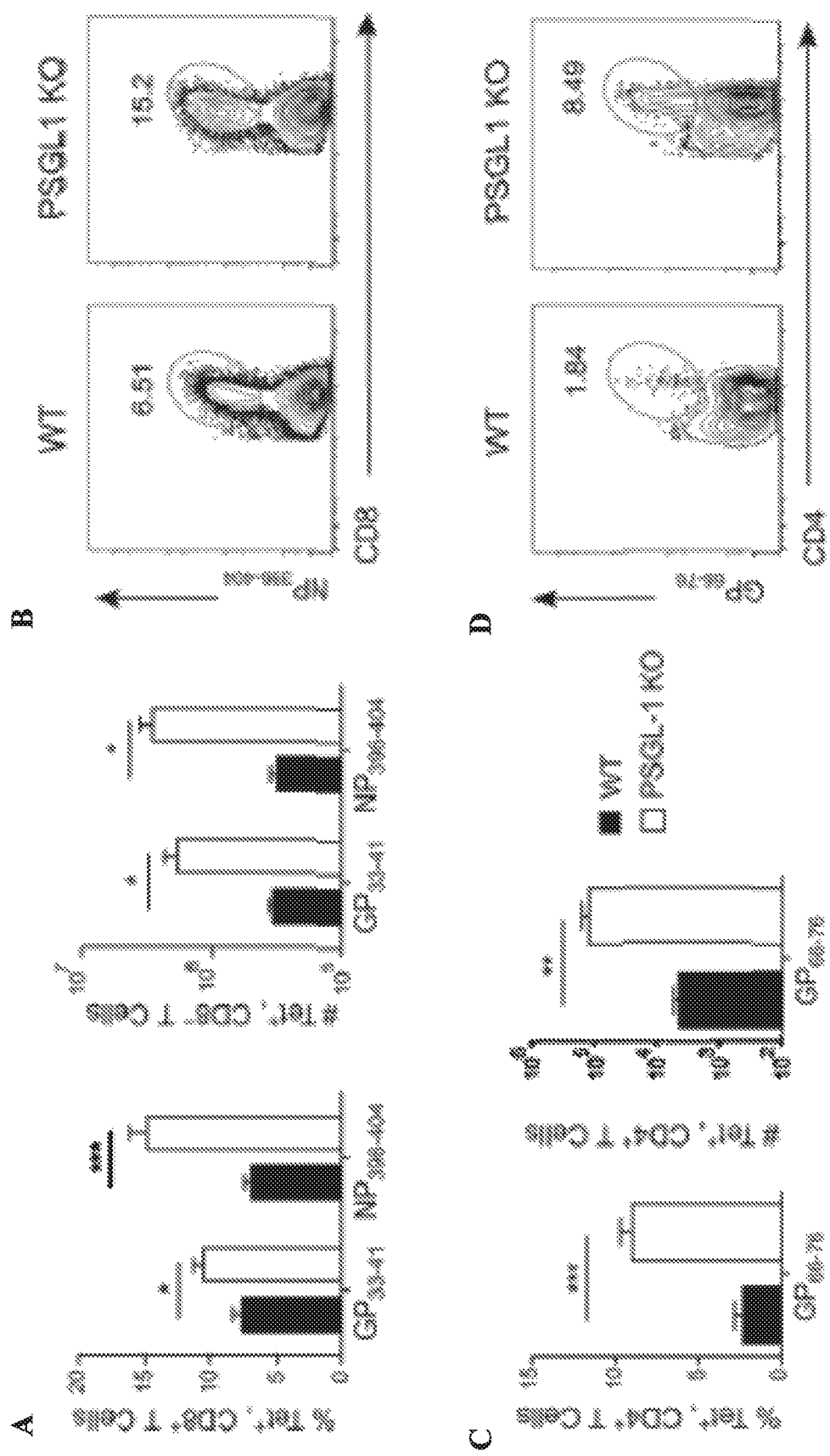
FIGS. 9A-D show that PSGL-1 KO virus-specific T cells effectively migrate and accumulate in lung. (A-D) cells from WT (black bars) or PSGL1-K0 (white bars) mice lungs at day 7.5 dpi stained with $D^bGP_{33-41}$ tetramers or $D^bNP_{396-404}$ tetramers (A-B) or $IA^b\text{-}GP_{66-76}$ (C-D).

Since engagement of PSGL-1 on T cells by E- and P-selectin on endothelium can be important for migration to sites of inflammation, CD8+ T cell accumulation in the blood and spleen in PSGL-1-deficient mice could result from impaired migration to peripheral sites. The lung, which represents an alternate site of infection that, unlike the spleen, requires adhesion receptor regulation for T cell entry was examined. Consistent with findings in the spleen, virus-specific CD8+(FIG. 9a,b) and CD4+ T cells (FIG. 9c,d) in the lungs of PSGL-1-deficient mice accumulated to a greater extent than in WT mice. The results show that in PSGL-1-deficient mice, virus-specific T cells are preserved in strikingly higher numbers than are WT cells.

Example 2

PSGL-1-Deficient CD8+ T Cells have Enhanced Survival

Figures 2A, 2B, 2C, 2D, 2E:
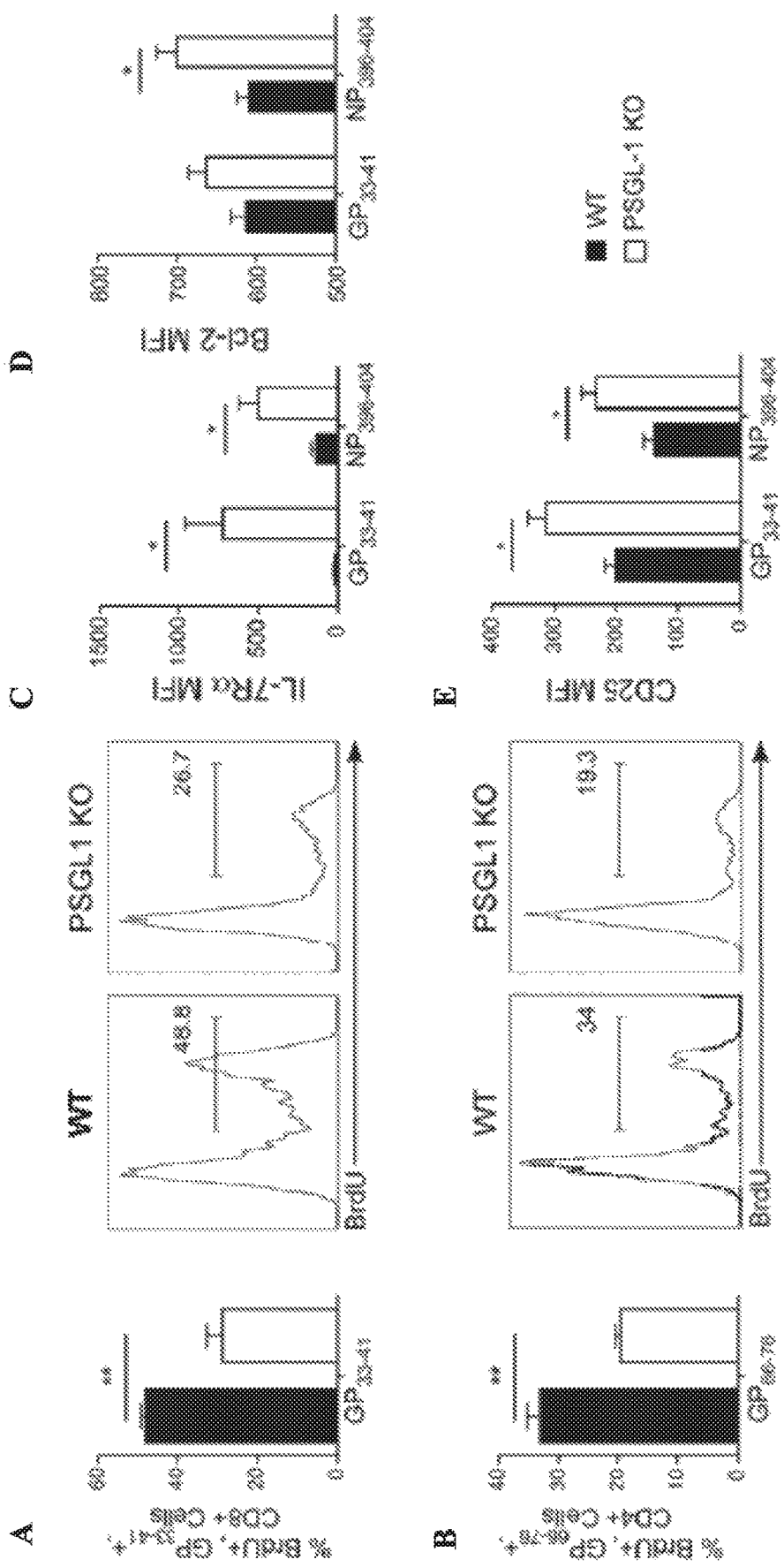
FIGS. 2A-E show that virus-specific PSGL-1 KO T cells display enhanced survival but not proliferation. WT mice are represented by black bars and PSGL-1 KO mice are represented by white bars. (A-B) Levels of $GP_{33-41}$+CD4+ cells (A) and $GP_{66-76}$+CD4+ cells (B) from WT and PSGL-1 spleens isolated at 8-dpi (C-D) Levels of IL7Rα (C) and Bcl-2 (D) from WT and PSGL-1 spleens isolated at 10-dpi (E) Levels of CD25 from WT and PSGL-1 blood at 10-dpi.
Figures 10A, 10B, 10C, 10D, 10E:
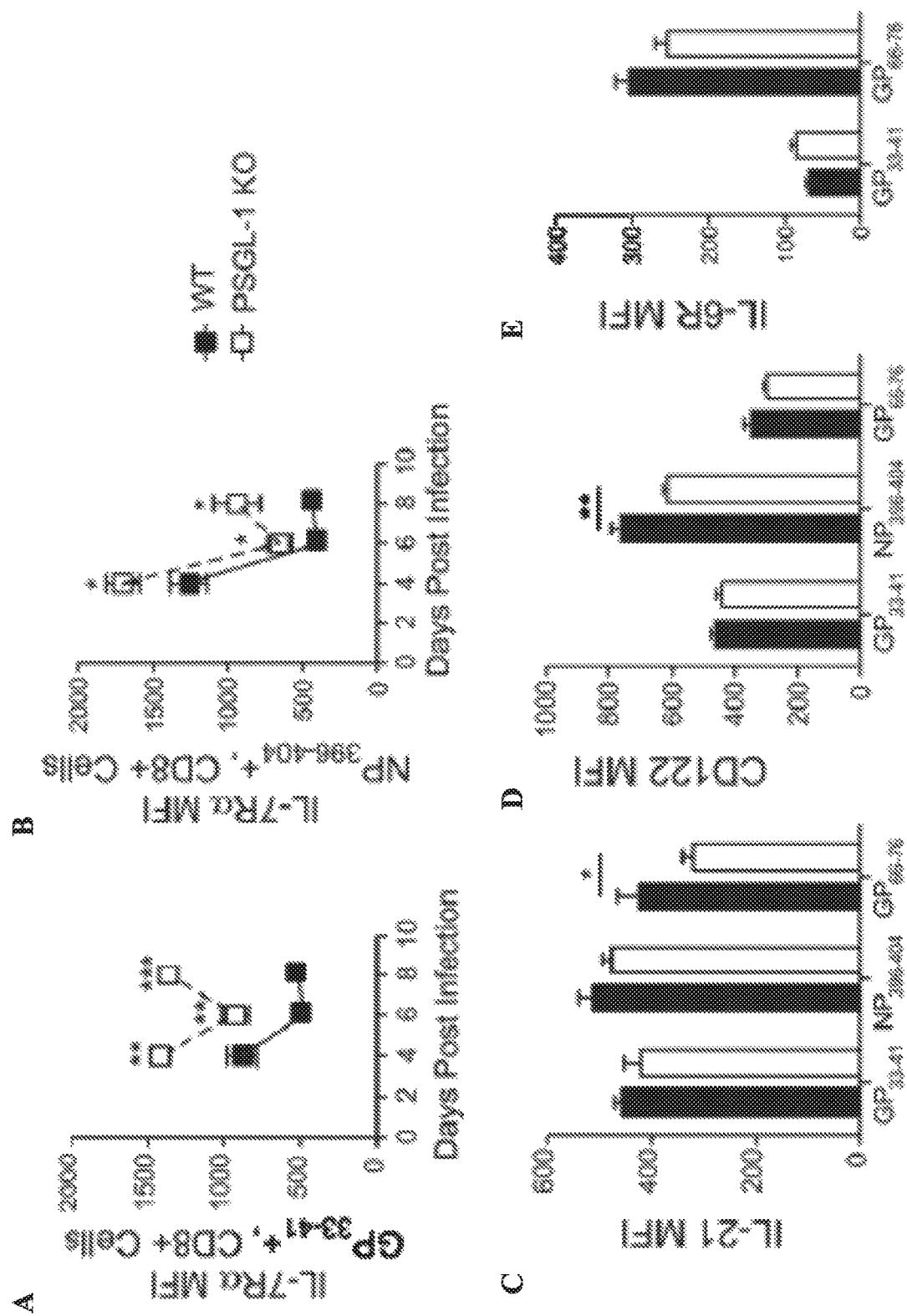
FIGS. 10A-E show cytokine receptor levels on virus-specific T cells. WT mice are represented by black squares or bars and PSGL-1 KO mice are represented by white squares or bars. (A) levels of IL-7Rα on $GP_{33-41}$ cells at 4, 6 and 8 dpi (B) levels of levels of IL-7Rα on $NP_{396-404}$ cells at 4, 6 and 8 dpi (C) levels of IL-21 at 9 dpi (D) levels of CD122 at 9 dpi (E) levels of IL-6R at 9 dpi.

Enhanced proliferation and/or survival could account for the accumulation of virus-specific T cells in PSGL-1-deficient mice. To assess proliferation, in vivo BrdU incorporation by virus-specific CD8+ T cells was analyzed at 8-dpi. BrdU labeled ~50% of WT $GP_{33-41}+CD8+$ T cells, but only ~25% PSGL-1-deficient $GP_{33-41}+CD8+$ T cells (FIG. 2a). Similarly, 2× more WT $GP_{66-76}$ CD4+ T cells incorporated BrdU than PSGL-1-deficient CD4+ virus-specific cells (FIG. 2b). Since division did not seem to account for greater numbers of PSGL-1-deficient CD8+ T cells, the expression levels of the survival molecules, IL-7Rα and its downstream signaling target Bcl2 by CD8+ effector cells was examined. At 10-dpi both $GP_{33-41}+$ and $NP_{396-404}+$ T cells from PSGL-1-deficient mice displayed increased levels of IL-7Rα (FIG. 2c) and Bcl-2 (FIG. 2d) compared to WT cells. Furthermore, IL-7Rα levels on PSGL-1-deficient virus-specific CD8+ T cells were higher than on WT cells throughout the expansion phase (FIG. 10a,b). CD25 levels on $GP_{33-41}+$ and $NP_{396-404}+$ T cells from PSGL-1-deficient mice were also increased (FIG. 2e), whereas receptors for other cytokines that can enhance T cell survival were similar or reduced, including IL-21R, CD122 and IL-6R (FIG. 10c-e). Together, these findings indicate that the accumulation of virus-specific CD8+ T cells in PSGL-1-deficient mice was most likely a result of enhanced survival.

Example 3

Figures 3A, 3B, 3C, 3D, 3E, 3F, 3G:
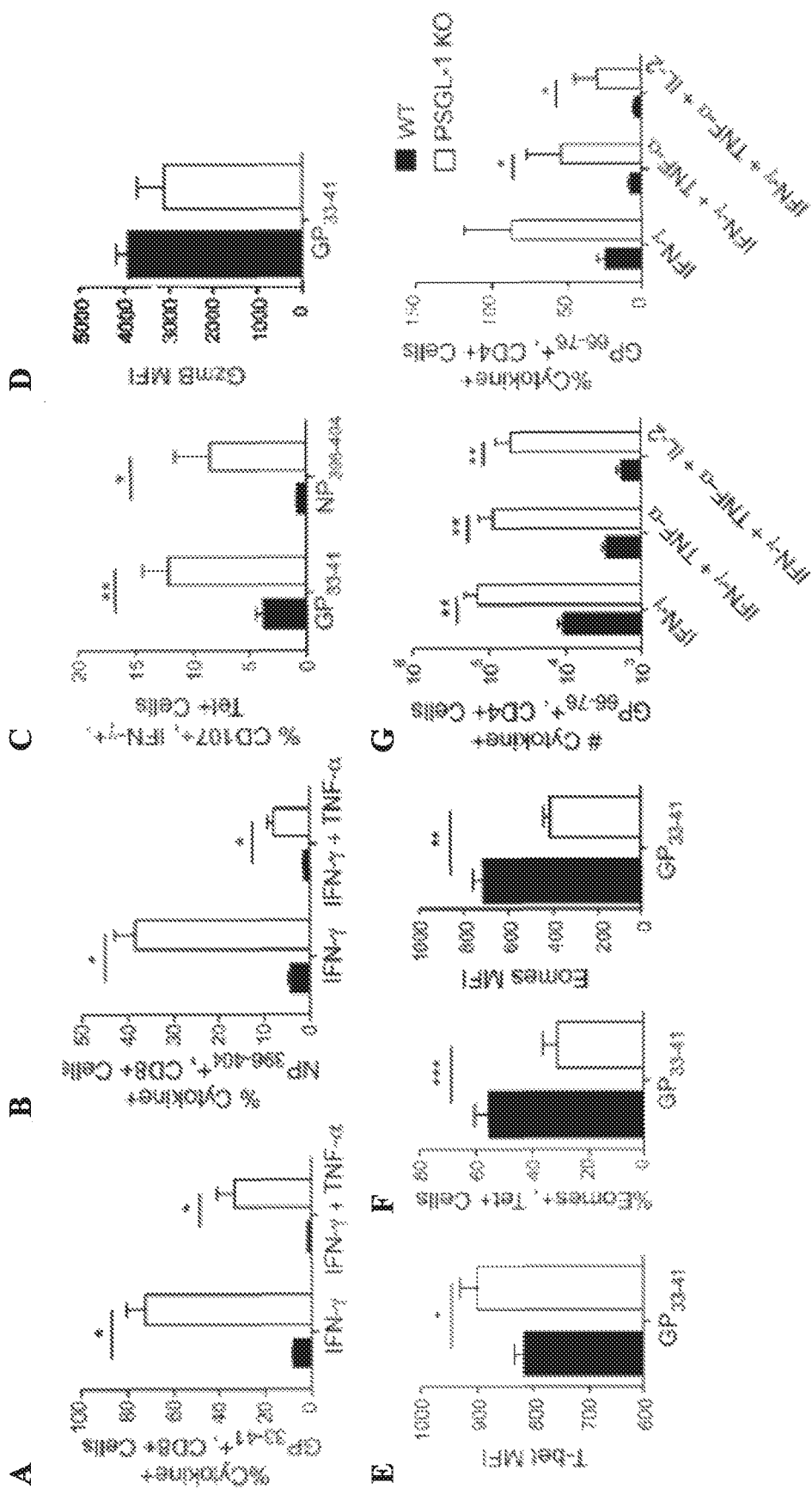
FIGS. 3A-G show enhanced effector T cell function in PSGL-1 KO mice. WT mice are represented by black bars and PSGL-1 KO mice are represented by white bars. (A) production of INF-γ and INF-γ+TNF-α in $GP_{33-41}$+ CD8+ cells. (B) production of INF-γ and INF-γ+TNF-α in $NP_{396-404}$+ CD8+ cells. (C) production of CD107+INF-γ+ Tet+ cells. (D) production of Granzyme B in $GP_{33-41}$+ CD8+ cells. (E) production of T-bet in $GP_{33-41}$+CD8+ cells. (F) production of Eomes in $GP_{33-41}$+ CD8+ cells. (G) production of INF-γ, INF-γ+TNF-α and INF-γ+TNF-α+IL-2 in $GP_{66-76}$+CD4+ cells.
Figures 11A, 11B, 11C, 11D, 11E:
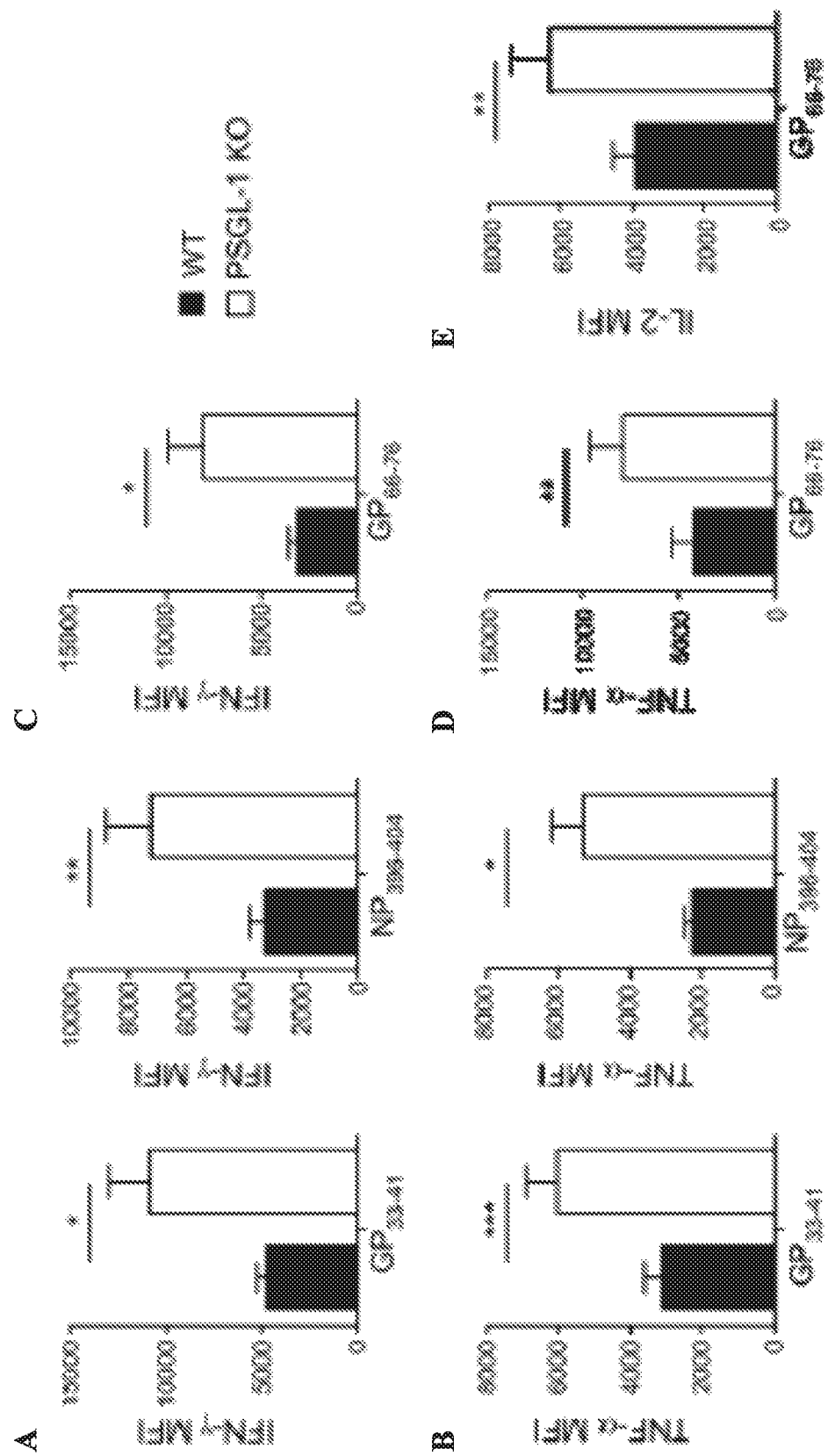
FIGS. 11A-E show that increased cytokine levels are expressed by effector T cells from PSGL-1 KO mice. WT mice are represented by black bars and PSGL-1 KO mice are represented by white bars. (A-C) production of INF-γ (A,C) and TNF-α (B) on CD8+ T cells at 10 dpi (D-E) production of TNF-α (D) and IL-2 (E) on CD4+ T cells at 10 dpi

Virus-Specific $CD4^+$ and $CD8^+$ T Cells in PSGL-1-Deficient Mice are Multifunctional Effectors Since chronic virus infection in WT mice leads to sequential loss of the CD8+ T cell capacity to produce IFN-γ, TNF-α, and IL-2, as well as to produce more than one of these cytokines simultaneously, cytokine production was examined. Much higher frequencies of PSGL-1-deficient $GP_{33-41}+$ T cells secreting IFNγ and IFN-γ+TNF-α together were found compared to WT cells (FIG. 3a). $NP_{396-404}+$ T cell responses were also functional (FIG. 3b). On a per cell basis, ~10% of $GP_{33-41}+$ T cells produced IFN-γ in WT vs ~70% in PSGL-1-deficient mice (FIG. 3a). Furthermore, virus-specific PSGL-1-deficient CD8+ T cells produced significantly higher levels of cytokines (FIG. 11a,b). Both $GP_{33-41}+$ and $NP_{396-404}+$ PSGL-1-deficient CD8+ T cells had enhanced CD107a levels, indicating better cytotoxic degranulation, together with IFN-γ section (FIG. 3c), although WT and PSGL-1-deficient $GP_{33-41}+CD8+$ T cells did not differ with respect to levels of granzyme B (Gzmb) protein (FIG. 3d).

Transcriptional programs differ in acute vs chronic LCMV infection. While T-bet is important in regulating CD8+ T cell effector and memory differentiation during acute infections, during Cl13 infection exhausted CD8+ T cells have reduced T-bet expression, which acts to sustain PD-1 levels. Since T-bet can directly bind the Pdcdl gene that encodes PD-1 and represses its expression, T-bet levels were examined in virus specific CD8+ T cells and found increased expression in $GP_{33-44}+$ T cells in PSGL-1-deficient mice at 10-dpi compared to WT cells (FIG. 3e). Furthermore, high Eomes levels, which mark terminally differentiated CD8+ T cells destined to die in WT Cl13 infected mice, were reduced in $G_{P33-41}+$ T cells in PSGL-1-deficient mice (FIG. 3f). Thus, while CD8+ T cells in WT mice develop exhaustion during Cl13 infection, in PSGL-1-deficient mice they instead generate multifunctional effectors.

The importance of CD4+ T cells during persistent infection is highlighted by the failure of. CD4+ T cell-depleted Cl13 infected mice to control viremia. Improved functionality with respect to cytokine production was also observed with GP$_{66-76}$+CD4+ cells (FIG. 3g, FIG. 11c-e). Not only did more virus-specific CD4+ T cells from PSGL-1-deficient mice produce elevated IFN-γ, TNF-α, and IL-2 compared to those from WT mice and these virus-specific CD4+ T cells were multifunctional with increased numbers of double/triple cytokine producers (FIG. 3g) that also produced higher levels of cytokines (FIG. 11c-e). These findings demonstrate that greater numbers of functionally superior virus-specific CD4+ T effector cells develop in PSGL-1-deficient mice than in WT mice after Cl13 infection.

Example 4

PSGL-1-Deficient T Cells have Reduced Inhibitory Receptor Expression

Figures 4A, 4B, 4C, 4D:
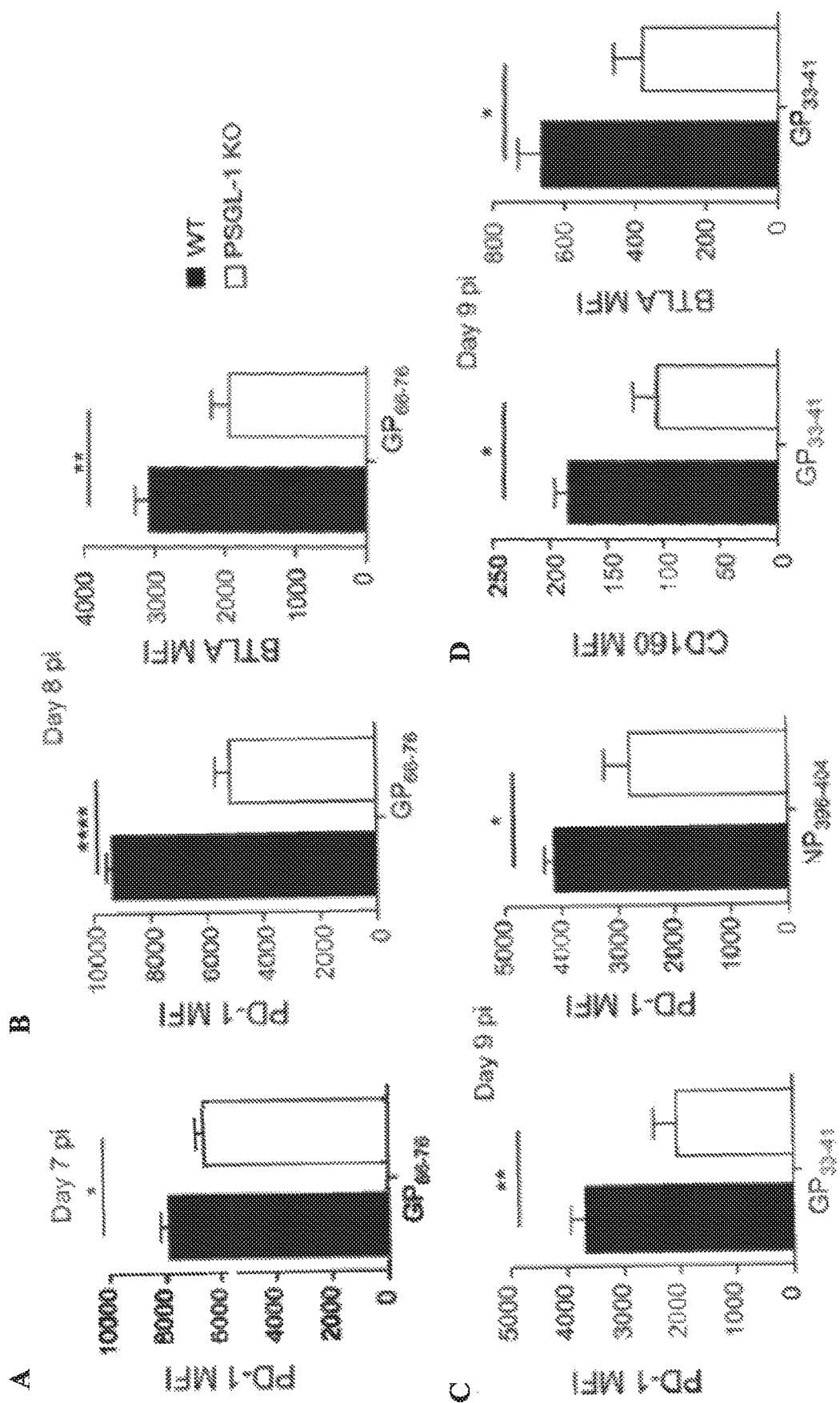
FIGS. 4A-D show inhibitory receptor expression on virus-specific T cells. WT mice are represented by black bars and PSGL-1 KO mice are represented by white bars. (A) levels of PD-1 on virus specific $GP_{66-76}$+ CD4+ T cells 7 dpi (B) levels of PD-1 on virus specific $GP_{66-76}$+CD4+ T cells 8 dpi (C) levels of PD-1 on virus specific $GP_{33-41}$+ CD8+ cells and $NP_{396-404}$+CD8+ cells 8 dpi (D) levels of CD160 and BTLA on virus specific $GP_{33-41}$+CD8+ cells.
Figures 12A, 12B, 12C, 12D, 12E:
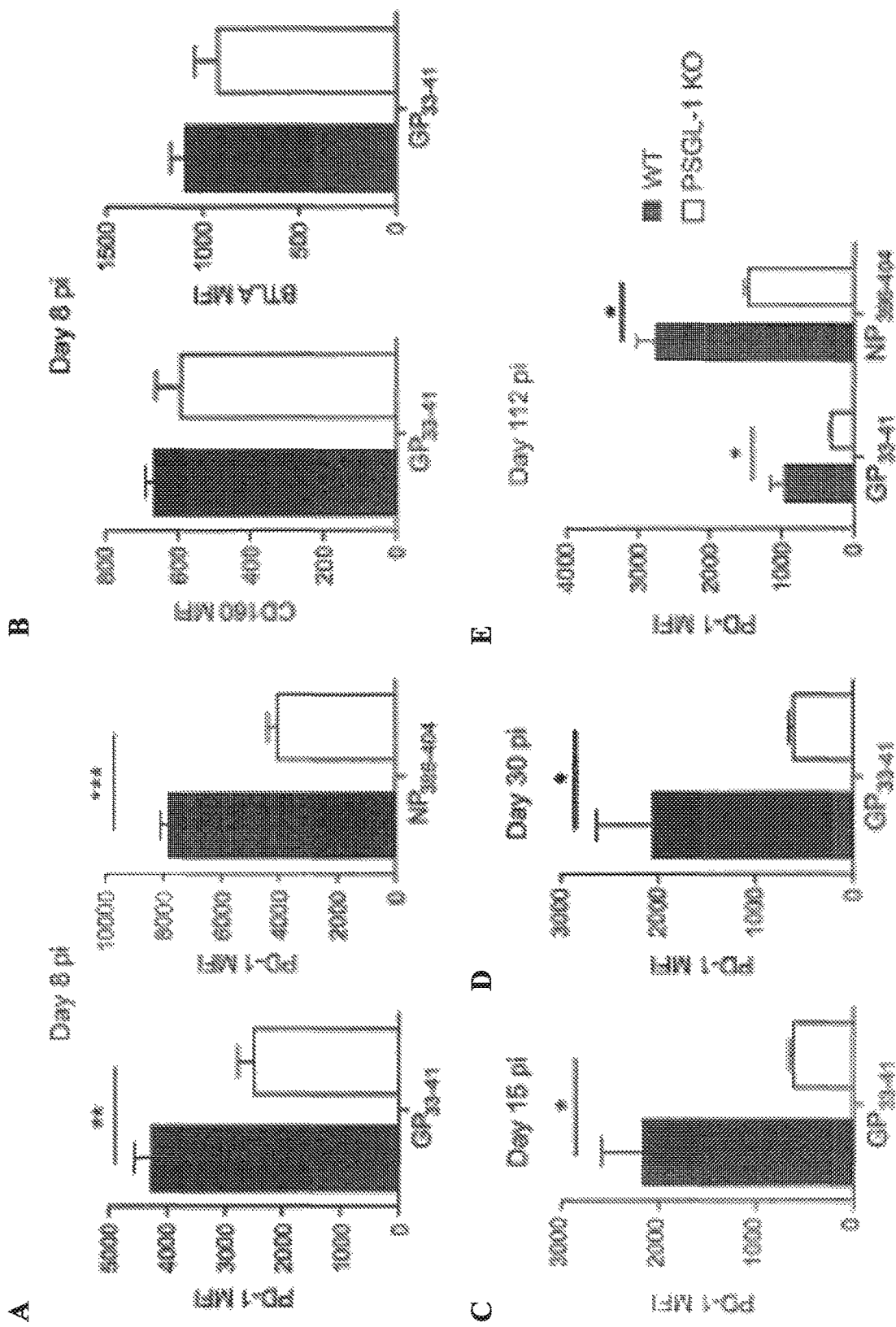
FIGS. 12A-E show inhibitory receptor expression on virus-specific T cells. WT mice are represented by black bars and PSGL-1 KO mice are represented by white bars. (A-E) levels of PD-1, CD160, and BTLA on virus-specific $GP_{33-41}$– and $NP_{396-404}$– CD8+ T cells at day 8 pd. in spleen (A-B), in blood at day 15 dpi (C), 30 dpi (D), and in spleen at day 112 dpi (E).

Since T cell exhaustion is in part a consequence of expression of multiple inhibitory molecules including PD-1, CD1 60, Lag-3, and BTLA, these receptors were examined on virus-specific T cells in WT and PSGL-1-deficient mice after infection. It was found that PD-1 levels on virus-specific GP$_{66-76}$+CD4+ T cells began to decrease by 7-dpi in PSGL-1-deficient mice, and further decreased on day 8 (FIG. 4a, b). At this time, BTLA levels were also diminished on PSGL-1-deficient CD4 T cells (FIG. 4b). Likewise, compared to WT, PSGL-1-deficient CD8+ T cells expressed lower levels of PD-1, but similar levels of CD160 and BTLA at 8-dpi (FIG. 12a,b). PSGL-1-deficient virus-specific CD8+ T cells showed diminished expression of all three receptors by 9-dpi (FIG. 4c,d). Furthermore, PD-1 downregulation was sustained at 15-, 30-, and 112-dpi (FIG. 12c-e). These findings indicate that although not coordinately regulated, reduced inhibitory receptor levels are correlated with functionality in virus-specific CD4+ and CD8+ T cells in PSGL-1-deficient mice after Cl13 infection.

Example 5

The Accumulation of Virus-Specific PSGL-1-Deficient T Cells is Cell-Intrinsic

Figures 5A, 5B, 5C, 5D, 5E, 5F, 5G:
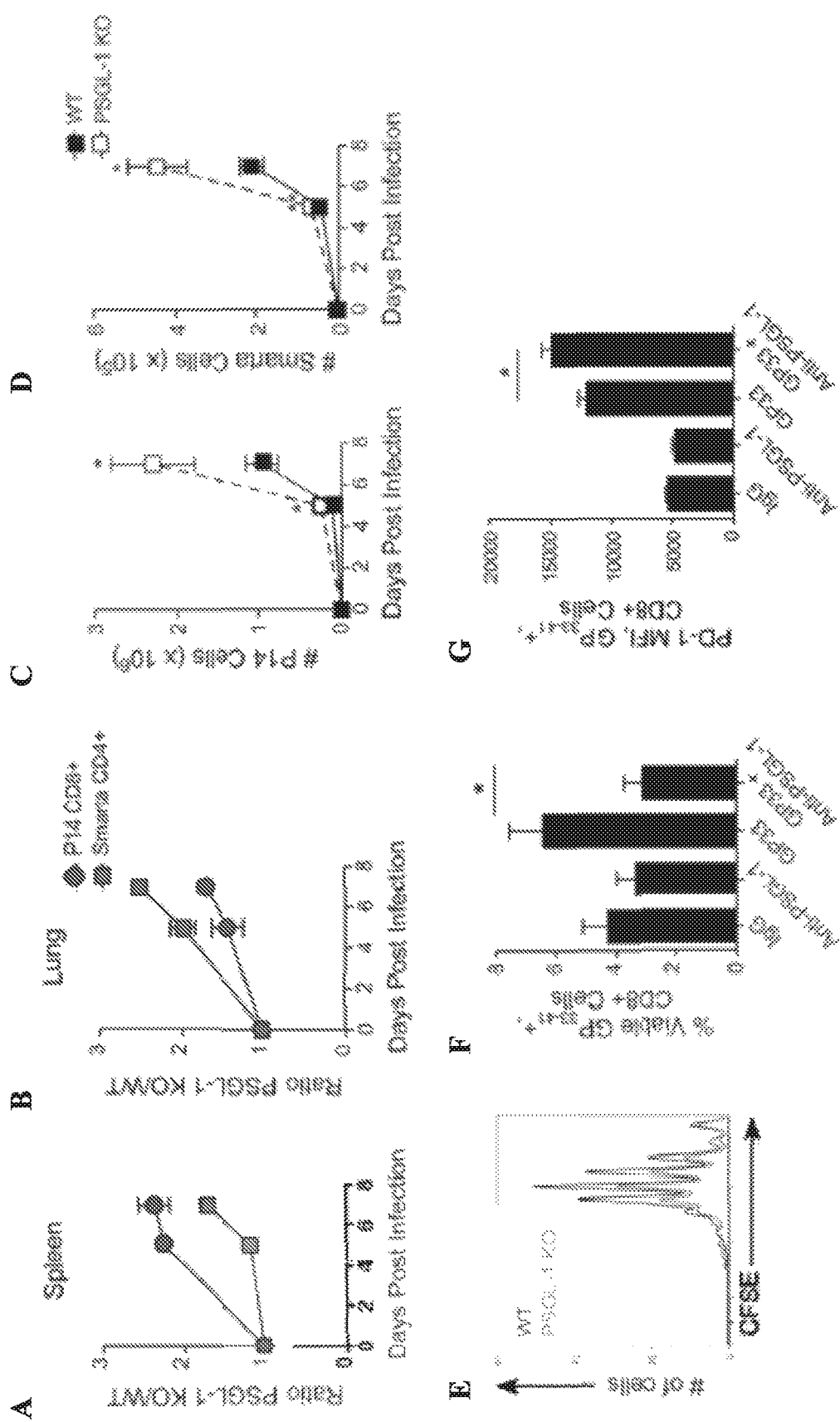
FIGS. 5A-G show that the accumulation of PSGL-1 KO virus-specific $CD8^+$ and $CD4^+$ T cells is cell intrinsic and PSGL-1 ligation of exhausted $CD8^+$ T cells diminished their survival. WT and PSG-L-1 KO naïve P14 transgenic T cells are represented by circles or 1PSGL-1 KO naive Smarta transgenic $CD4^+$ T cells are represented by squares. (A-B) ratio of PSGL-1 KO to WT in spleen (A) or lung (B) from WT and PSG-L-1 KO naive P14 transgenic T cells (circles) or 1PSGL-1 KO naïve Smarta transgenic $CD4^+$ T cells (squares) 1 dpi (C-D) the number of WT (circles) and PSGL-1 KO (squares) P14 cells (C) or Smarta cells (D) in spleen 1 dpi (E) CFSE dilution in WT or PSGL-1 KO P14 cells at 2-dpi (F-G) frequency of propidium negative $GP_{33-41}$+ CD8+ T cells (F) and PD-1 levels on $GP_{33-41}$+ CD8+ T cells (G) from splenocytes isolated at 9-dpi.
Figures 13A, 13B, 13C, 13D, 13E:
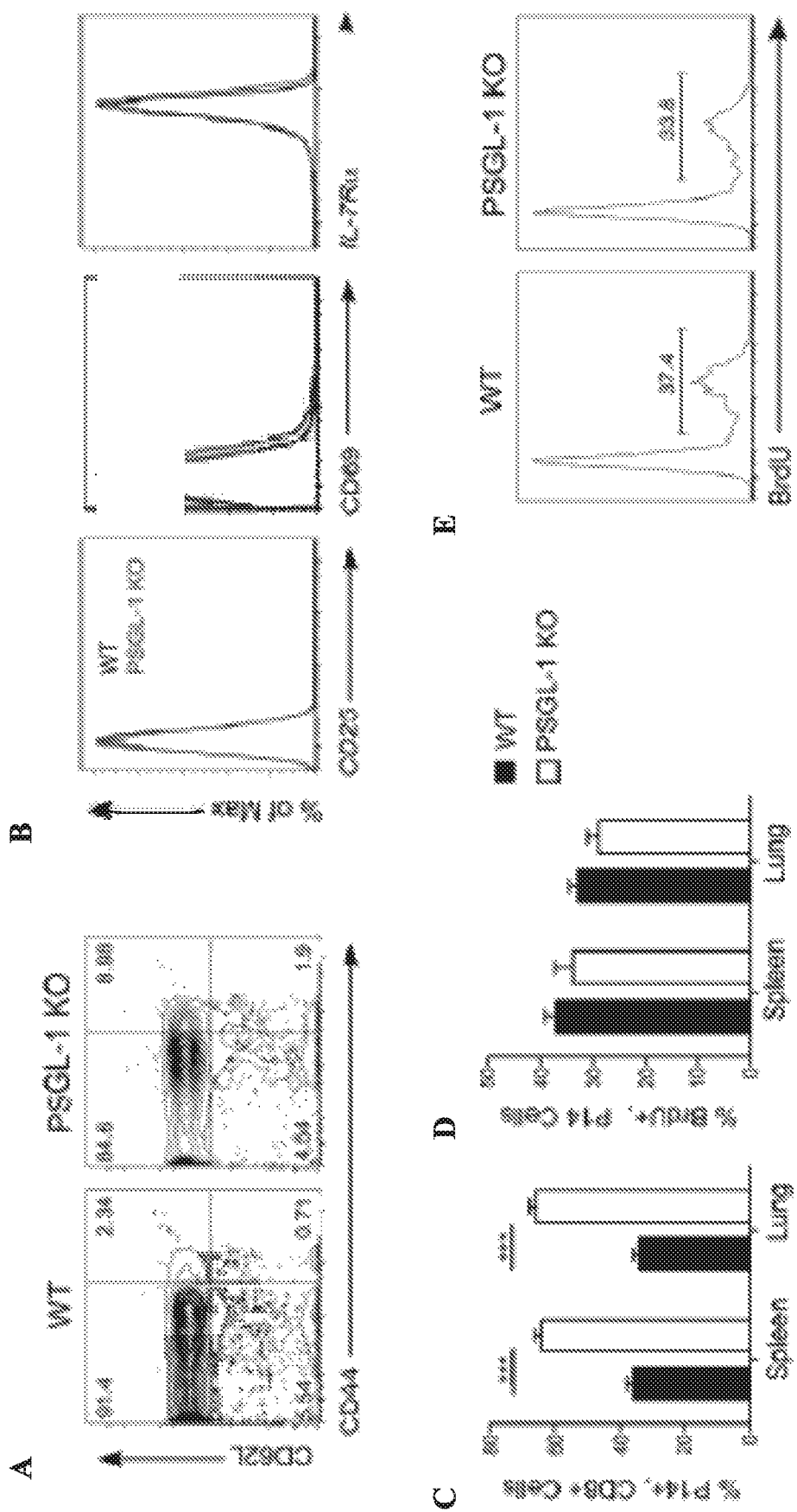
FIGS. 13A-E show pre-infection phenotype of naive WT and PSGL-1 KO P14 cells and proliferation WT and PSGL-1 KO P14 cells. WT mice are represented by black bars and PSGL-1 KO transgenic P14+ Tg mice are represented by white bars. (A-B) spleens stained with CD44 and CD62L (A) and CD25, CD69, and CDl27 (B). (C) frequency of WT or PSGL-1 KO P14 cells in spleen and lung at day 13 dpi (D) Brdu incorporation in spleen and lung at day 13 dpi (E) representative histograms in spleen.

To address which features of the improved response to Cl13 in PSGL-1-deficient mice were intrinsic to T cells, WT and PSGL-1-deficient TCR transgenic CD8+P14 cells, which are specific for the GP$_{33-41}$ epitope of LCMV, were used and transferred these cells to WT hosts. The activation state of WT and PSGL-1-deficient P14 cells was examined directly ex vivo and found similar expression levels of CD44 and CD62L (FIG. 13a), and of CD25, CD69, and IL-7Rα (FIG. 13b). Then WT and PSGL-1-deficient P14 cells were co-transfected at a 1:1 ratio into WT hosts and infected the mice with Cl13 one day later. An increased ratio of PSGL-1-deficient P14 cells to WT P14 cells was found in the spleen (FIG. 5a) and lung (FIG. 5b) at 5- and 7-dpi. This increase was also reflected by greater numbers of PSGL-1-deficient P14 cells in spleens (FIG. 5c) and increased frequencies in the spleen and lungs at 13-dpi (FIG. 13c). This accumulation was not a result of increased proliferation as measured by BrdU incorporation at 8-dpi (data not shown) and 13-dpi (FIG. 13d,e), supporting the concept that PSGL-1-deficient T cells survived better than WT cells. Furthermore, CFSE dilution in WT and PSGL-1-deficient P14 cells was identical at 2-dpi, in fact at this time WT cells had a slight accumulation advantage (FIG. 5e). Despite the greater accumulation, PSGL-1-deficient cells, not unexpectedly, displayed an exhausted phenotype (decreased cytokine production and high PD-1) when responding in the WT environment with Cl13 infection (data not shown). Thus, although the accumulation of PSGL-1-deficient virus-specific CD8+ T cell was cell-intrinsic, their functional restoration is dependent on additional factors in the PSGL-1-deficient environment. Next, the function of PSGL-1 in virus-specific CD4+ cells was examined with WT and PSGL-1-deficient transgenic Smarta CD4+ T cells. When co-transferred to WT mice, an increased ratio of PSGL-1-deficient to WT cells was observed on 5- and 7-dpi in spleen (FIG. 5a) and lungs (FIG. 5b) after infection, with parallel increased numbers (FIG. 5d). Despite having a cell-intrinsic survival, both CD8+ and CD4+ PSGL-1-deficient effectors fail to be functionally rescued in a WT environment.

Example 6

PSGL-1 Ligation Decreases Survival of Exhausted CD8$^+$ T Cells

To determine the impact of PSGL-1 ligation on virus-specific CD8+ T cells, splenocytes from WT mice were isolated at 9-dpi, a point when CD8+ T cells are functionally exhausted. A ~7% viable tetramer+CD8+ T cells was found after 4 days of GP$_{33-41}$ stimulation (FIG. 5f). When splenocytes were stimulated with GP$_{33-41}$ peptide in the presence of anti-PSGL-1 antibody, tetramer CD8+ T cells survival decreased by ~50%, to levels similar to those in cultures with media containing only IgG or anti-PSGL-1 (FIG. 5f). PD-1 levels were increased after peptide stimulation, and these levels were further elevated when, anti-PSGL-1 was present during peptide stimulation (FIG. 5g). These results show that PSGL-1 ligation during antigen stimulation limits the survival of virus-specific CD8+ T cells and can enhance their PD-1. expression.

Example 7

Figures 6A, 6B, 6C, 6D, 6E:
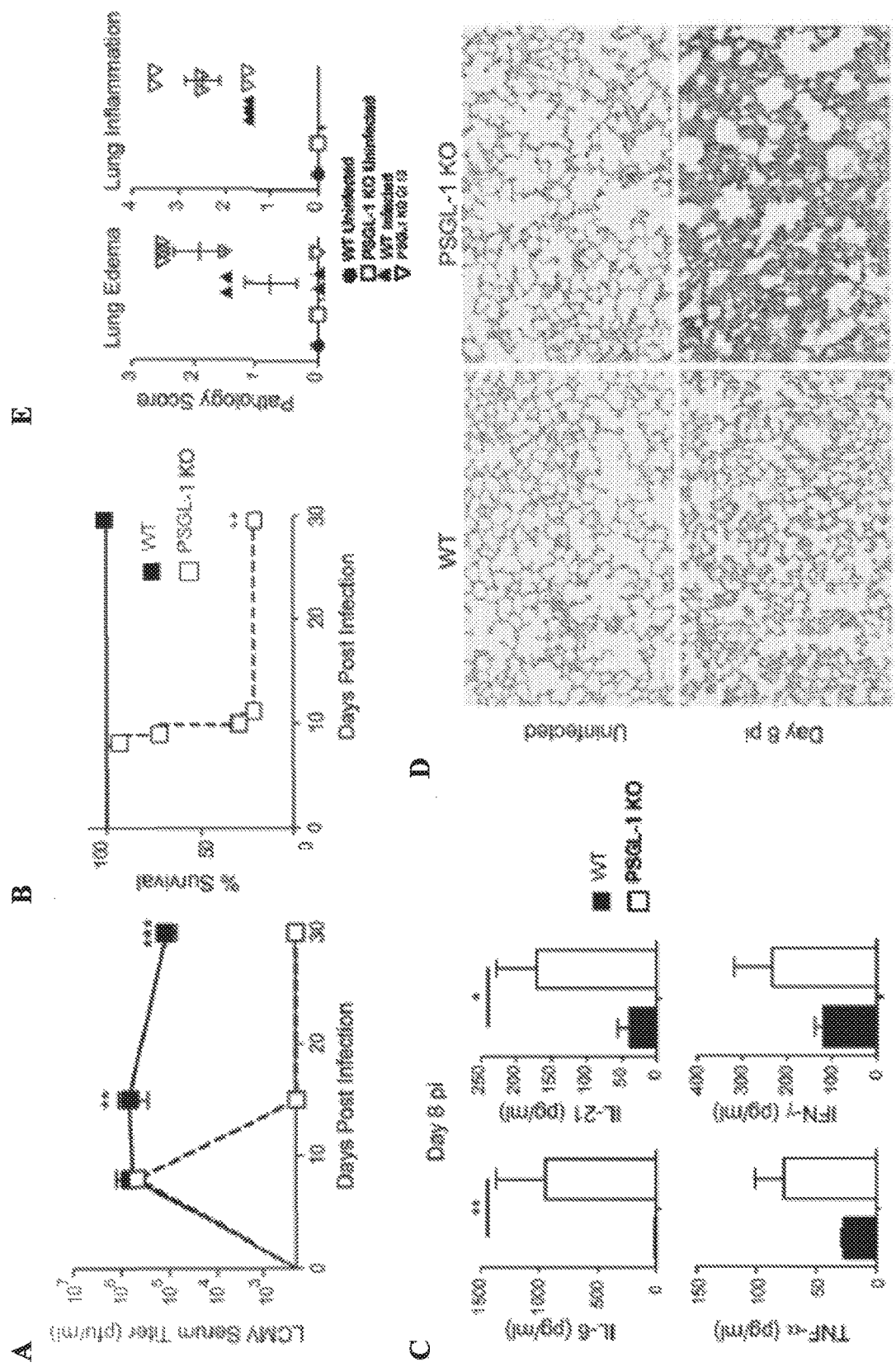
FIGS. 6A-E show that PSGL-1 KO mice have accelerated viral control and extensive immunopathology. (A-C) serum LCMV viral levels (A), survival curves (B) and serum kinase levels (C) from WT mice represented by black circles or black bars and PSGL-1 KO mice represented by white squares or white bars at 8-dpi (D) H&E histology of uninfected and day 8 infected WT and PSGL-1 KO lungs. (E) Pathology scores in lungs for WT and PSGL-1 KO uninfected and 8-dpi.
Figures 14A, 14B:
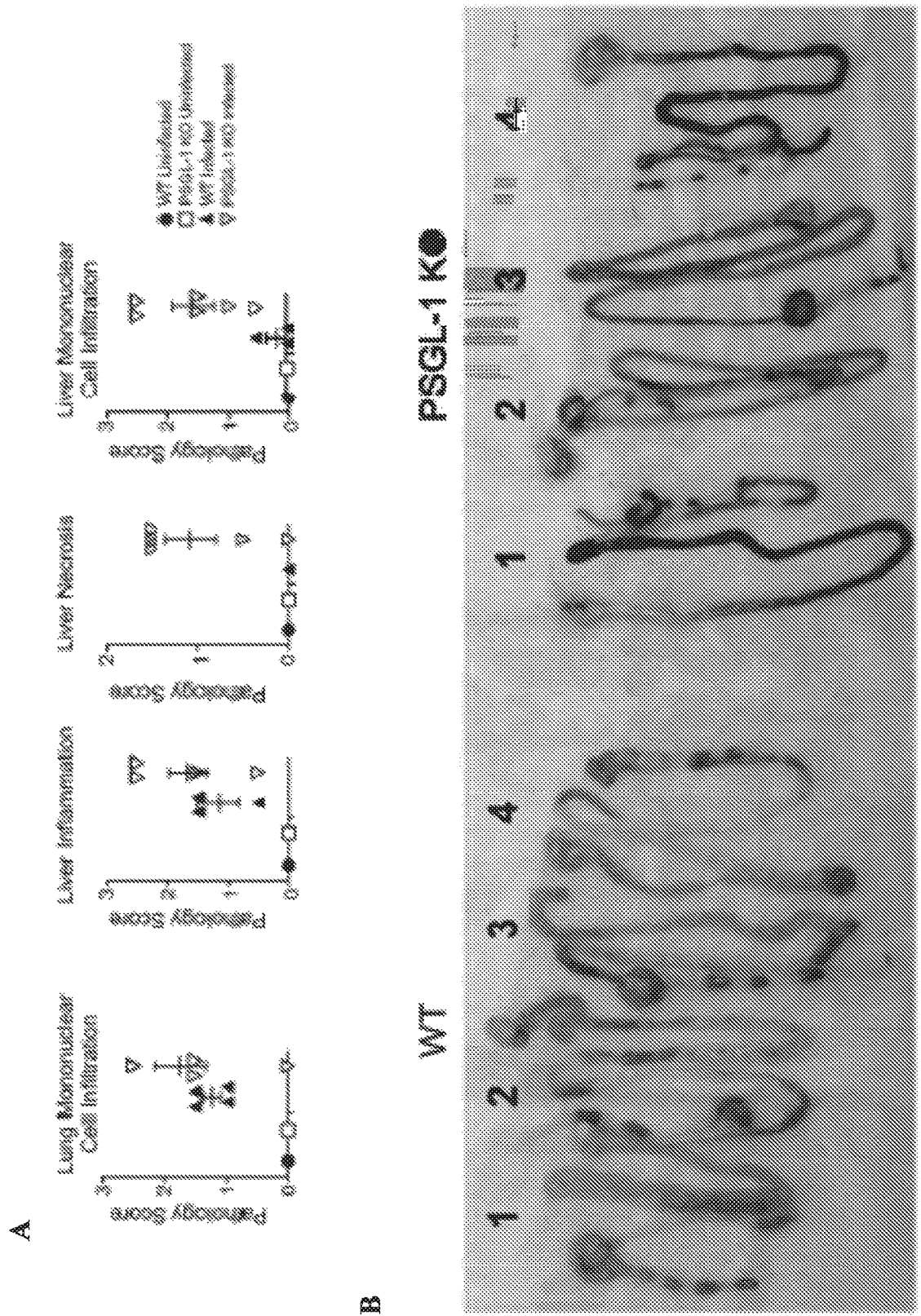
FIGS. 14A-B show greater pathology in PSGL-1 KO mice. WT uninfected mice are represented by black circles, PSGL-1 KO uninfected mice are represented by white bars squares, WT infected mice are represented by black triangles, PSGL-1 KO infected mice are represented by white triangles mice. (A) pathology scores for WT and PSGL-1 KO lung and liver. (B) stomach, small and large intestines isolated from WT and PSGL-1 KO mice at day 9 dpi.

PSGL-1-Deficient Mice Clear Chronic LCMV Control but Show Enhanced Immunopathology Since improved functional CD4+ and CD8+ T cell responses together with decreased immune inhibitory receptor expression was observed in PSGL-1-deficient mice compared to WT, the ability of PSGL1-deficient mice to control the Cl13 virus was examined. It was found that compared to WT mice, which had elevated viremia to 30-dpi, PSGL-1-deficient mice cleared the virus from blood by 15-dpi (FIG. 6a). However, the improved anti-viral T cell response was associated with >50% mortality, with death beginning at 8-dpi (FIG. 6b). To address systemic inflammation, proinflammatory cytokines were examined and observed that PSGL-1-deficient mice had dramatically elevated serum levels of IL-6, IL-21, TNF-α, and IFN-γ (FIG. 6c). Furthermore, lung immunopathology which included lung infiltrates (FIG. 6d, FIG. 14a), edema, and inflammation at 8-dpi (FIG. 6d,e) was increased in PSGL-1-deficient infected mice. Elevated pathology was also evident in the kidneys, livers, and intestines (FIG. 14a,b). Thus, although PSGL-1-deficient mice controlled viral replication much more effectively than WT mice, this results in extensive inflammation and increased mortality due to immunopathology. Therefore, PSGL-1 functions to limit an overly exuberant effector response.

Example 8

Optimal Virus-Specific CD8+ T Cell Function in PSGL-1-Deficient Mice Requires CD4+ T Cells Increases in $GP_{66-76}$+CD4+ T cells were observed in PSGL-1-deficient mice by 5-dpi and with further increasing accumulation to 9-dpi (FIG. 7a), consistent with a role for. PSGL-1 deficiency in CD4+ T cells in impacting CD8 T cell response. To examine their contribution, CD4+ T cells from PSGL-1-deficient mice were depleted by administering anti-CD4 antibody. The CD8+ T cell responses to Cl13 were compared to those of PSGL-1-deficient CD8+ T cells from mice treated with a control antibody, or of WT T cells. It was found that CD4+ T cell-depleted PSGL-1-deficient mice had reduced frequencies of $GP_{33-41}$+ and $NP_{396-404}$+CD8+ T cells to levels found in WT mice (FIG. 7b). Furthermore, they had reduced numbers of IFN-γ and IFN-γ+TNF-α+ CD8+ T cells compared to PSGL-1-deficient mice that had CD4+ T cells at 10-dpi (FIG. 7c). This was mirrored by changes in PD-1 levels on $GP_{33-41}$+ and $NP_{396-404}$+ T cells, which remained elevated and were to similar levels on WT cells (FIG. 7d). Unlike PSGL-1-deficient mice in which serum Cl13 levels were reduced at 10-dpi, in CD4+ T cell depleted mice, the virus levels remained comparable to those in WT mice (FIG. 7e), whereas the titers in PSGL-1-deficient mice were decreasing at this time Furthermore, mortality of PSGL-1-deficient mice after 10-dpi was prevented in CD4+ T cell depleted mice (FIG. 7e). These results show that for virus-specific PSGL-1-deficient CD8+ T cells to escape functional exhaustion, they require help from CD4+ T cells. Thus by their improved numbers and function, it was determined that CD4+ T cells modulate CD8+ T cell function in the context of PSGL-1 deficiency.

Example 9

Materials & Methods

Mice. C57BL/6.1 mice and Selplg-/- mice were purchased from the Jackson laboratories. Mice were bred and maintained in specific pathogen-free facilities and were infected in conventional BSL-2 facilities at the Sanford-Burnham Medical Research Institute. Selplg-/- mice were backcrossed to C57BL/6J mice for more than 10 generations. PI4 and Smarta TCR transgenic mice were obtained from Charles D. Surh (The Scripps Reseach Institute). These mice were bred to Ly5.1 (B6.SJL-Ptprc$^a$ Pepc$^b$/BoyJ) mice and to Thy1.1 (B6.PL-Thy 1$^a$/CyJ), Selplg-/- mice. Mice used for experiments were at least six weeks of age. Experiments were in compliance with the Sanford-Burnham Medical Research institute IACUC regulations and veterinarian-approved.

Infection, Proliferation, and Cell Transfer.

LCMV Cl13 strain was propagated in baby hamster kidney cells and titrated on Vero African green monkey kidney cells. Frozen stocks were diluted M Vero cell media and $2\times10^6$ plaque-forming units (PFU) of LCMV Cl13 were injected i.v. To assess proliferation mice were injected i.p. with 2 mg of BrdU (Sigma-Aldrich) 16 hr before isolating lymphocytes from the spleens and lungs at days 8 or 13 after infection. For adoptive transfer, WT P14 and PSGL-1 KO P14 cells were purified (Stemcell Tech) and $1\times10^3$ cells were transferred i.v. into WT mice that were infected with LCMV Cl13, 1 day later.

Flow Cytometry and Staining.

Cells were surface stained for 20 min at 4° C. or 1 hr 15 min at room temperature for tetramer staining in PBS supplemented with FACS staining buffer (2% FBS and 0.01% sodium azide). The following antibodies from Biolegend were used: anti-CD8α (clone 53-6.7), anti-PD-1 (clone RMP1-30), anti-CD4 (clone GKI.5), anti-CD90.1 (clone OX-7), anti-CD45.1 (clone A20), anti-IL-21R (clone 4A9), anti-CD126 (clone D7715A7), anti-CD44 (clone IM7), anti-CD62L (clone MEL-14). The following clones were from eBioscience: anti-CD127 (IL-7Ra clone A7R34), anti-CD160 (clone ebiocnx-3), anti-BTLA (clone 6f7). The following antibodies were from BD: anti-CD122 (clone TM-(31), anti-BcI-2 (clone 3F11), anti-CD107 (clone 1D4B), anti-CD162 (clone 2PH1), anti-CD25 (clone 3C7), anti-CD69 (clone H12F3), anti-Vα2 (clone B20.1). The $H-2D^b$-$GP_{33-41}$, $H-2D^b$-$NP_{396-404}$ tetramers were purchased from Beckman Coulter. The $1A^b$-$_{66-77}$ tetramer was provided by the NIH core facility. Cells were washed twice with FACS staining buffer and fixed for 15 min with 1% formaldehyde in PBS. Cells were washed twice, and resuspended in FACS staining buffer. For intracellular cytokine staining, cells were fixed and perineabilized with the Cytofix/Cytoperm Kit (BD) and were stained with anti-GzmB (clone MHGBO5: invitrogen), anti-TNF-α (clone MP6-XT22: biolegend), anti-IFN-γ (clone XIVIG1.2: Biolegend), anti-IL-2 (clone JES6-5H4: eBioscience). BrdU staining was performed using a kit from eBioscience. For transcription factor detection, cells were fixed and permeabilized using the FoxP3 staining kit (eBioscience) and stained with anti-Tbet (clone 4B10: Biolegend), anti-Eomes (clone Dan11mag: eBioscience). Stained cells were analyzed on a LSRFortessa flow cytometer (BD).

Ex Vivo Peptide Stimulation.

$2\times10^6$ splenocytes from infected animals were seeded into 96-well round-bottom plates. The cells were stimulated in vita-o for 5 hrs at 37° C. with 2 pg/mL of $GP_{33-41}$, $NP_{396-404}$ or $GP_{61-80}$ peptides (AnaSpec), 50 U/mL IL-2 (NCI), and 1 µg/ml Brefeldin A (Sigma). Stimulated cells were then washed, surface stained, and then stained intracellularly. Ex vivo PSGL-1 ligation. $2\times10^6$ splenocytes from day 9 LCMV Cl13 infected animals were seeded into 96-well round-bottom plates. The cells were stimulated in vitro for 4 days at 37° C. with 50 U/mL IL-2 (NIH) in RPMI-1640 (Cellgro) media supplemented with 10 mM hepes (Cellgro), 1×MEM non-essential amino acids (Cellgro), 1 mM sodium pyruvate (Cellgro) and 10% heat-inactivated FBS (Hyclone), and the following conditions: 10 µg/mL rat IgG (JacksonImmuno Research), 10 µg/mL anti-PSGL-1 (4RAIO BioXCell), 2 pg/mL of $GP_{33-41}$ (AnaSpec), or anti-PSGL-1 (4RA10 BioXCell)+2 µg/mL of $GP_{33-41}$ (AnaSpec). Cultured cells were then washed, and stained with propidium iodide (1 µg/mL) for 10 min. at room temperature. Cells were washed and stained with anti-CD8αα, $H-2D-G_{P33-41}$ tetramer (Beckman Coulter), anti-PD-1 for 1 hr 15 min. at room temperature in FRCS staining buffer. Stained cells were analyzed on a LSRFortessa flow cytometer (BD) and live cells determined by excluding PI+ cells.

CFSE Labeling.

CD8+ T cells were negatively enriched from spleens of uninfected WT and PSGL-1 KO P14 TCR transgenic mice (Stemcell Tech). Equal numbers of purified WT and PSGL-1 KO P14 cells were pooled and labeled with 5 µM CFSE (Life Technologies) at 37° C. for 10 minutes, and washed with PBS. WT and PSGL-1 KO P14 cells were co-transferred at a 1:1 ratio ($1\times10^6$ cells of each) i.v. into WT recipients. WT hosts were infected with $2\times10^6$ PFU LCMV Cl 13 and CFSE dilution examined by FACS at day 2 dpi.

CD4 Depletion.

Mice received two 500 µg intraperitoneal injections of CD4-depleting antibody (clone GM 0.5, BioXCell) at day −1 and 0, and then infected with LCMV Cl13. Efficacy of CD4 depletion was confirmed in blood and spleens of treated mice.

Cytokines and Pathology.

Serum was isolated from WT and PSGL-1 KO mice at day 8 dpi and cytokine levels for IL-6, IL-21, TNF-α, and IFN-γ were examined using a multiplex 9-bead custom cytokine array (Millipore). Samples were analyzed on a Luminex IS200 instrument. Liver, kidney, and lungs were fixed in zinc formalin (z-fix Anatech), embedded in paraffin, and sectioned. Tissues were stained with H&E and digitally scanned using Aperio ScanScope. Pathology scoring was a blind assessment of tissue samples by a pathologist. Scores ranged from 0-3.5, with zero indicating no pathology and greater scores indicated increased pathology.

Data Analysis.

Flow cytometry data were analyzed using FlowJo software (TreeStar). Graphs were prepared using GraphPad Prism software.

Statistical Analysis.

GraphPad. Prism software was used to analyze experimental groups using a student t test, significance was set to $p<0.05$. A Mantel-Cox and Gehan-Breslow-Wilcoxon test was used to compare survival curves.

Example 10

Anti-Viral Responses

Figures 15A, 15B, 15C, 15D:
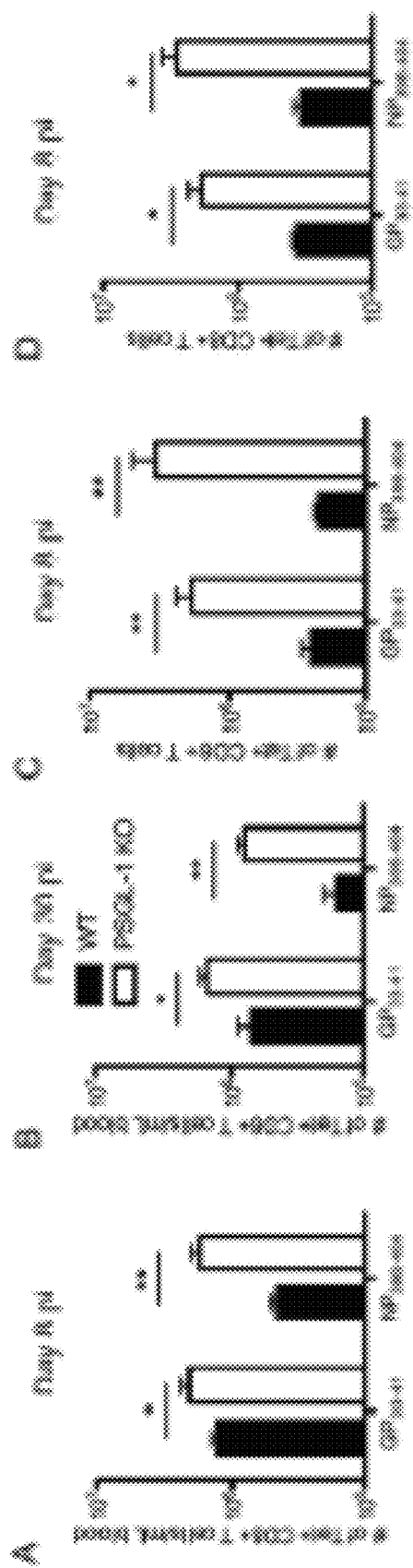
FIGS. 15 A-D show the accumulation of virus specific PSGL-1 KO T cells after Cl13 infection. (A-D) Virus specific CD8+ T cells were enumerated in blood at 8 dpi (A) and 30 dpi (B) post infection and in the spleen (C) and lung (D) at 8 dpi.
Figures 16A, 16B, 16C:
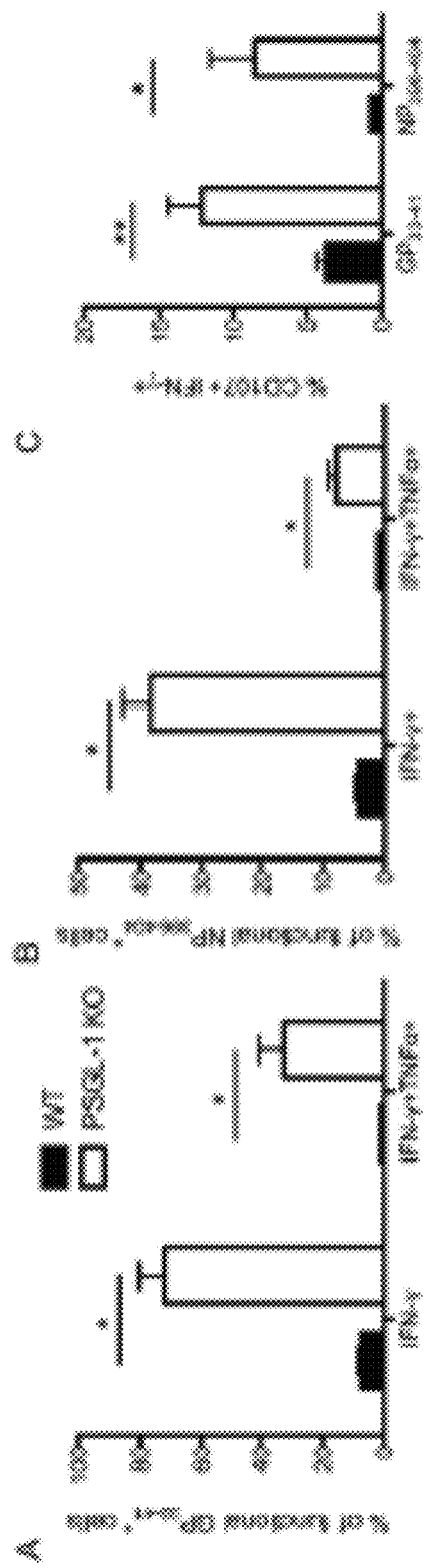
FIGS. 16A-C show enhanced anti-viral function of CD8+ T cells from PSGL-1 KO. (A-C) spleen cells stimulated with the $NP_{396-404}$ or $GP_{33-41}$ peptides and analyzed for IFN-γ and TNF-α (A, B) or CD107 (C).

In studies of the LCMV Cl13 virus that produces a chronic infection in mice, it was discovered PSGL-1 deficiency resulted in increased numbers of virus-specific CD8+ T cells after infection (FIG. 15A,B), that extended at least to d30 (FIG. 15C), indicating a lasting impact on T cells persistence. This finding is noteworthy for $NP_{396-404}$ Specific T cells which are deleted after Cl13 infection. This effect was due to improved T cell survival rather than increased expansion (not shown). Since PSGL-1 regulates leukocyte homing and LCMV infection is systemic, T cell recruitment to a peripheral site was tested, in this case the lungs, to see if there was an effect. However, there were greater numbers of virus-specific T cells in PSGL-1 KO than in WT mice (FIG. 15D) ruling out a general impairment of migratory capacity. CD8+ T cells progressively lose effector function after Cl13 infection, first the ability produce IL-2, TNF-α, and finally IFN-γ and CTL activity. In effective anti-viral responses, CD8+ T cells express multiple effector functions simultaneously. As shown in FIG. 16, both $GP_{33-41}$- and $NP_{396-404}$-specific T cells from PSGL-1 KO mice exhibited higher frequencies of IFN-γ+ and IFN-γ/ INF-α double+ cells than virus-specific CD8+ T cells from WT mice (FIG. 16A,B), indicating greater functionality. Cytotoxic degranulation in combination with IFN-γ production was also greater (FIG. 16C). The data demonstrate that PSGL-1 has an unexpected dampening effect on the CD8+ T cell responses.

Figures 17A, 17B:
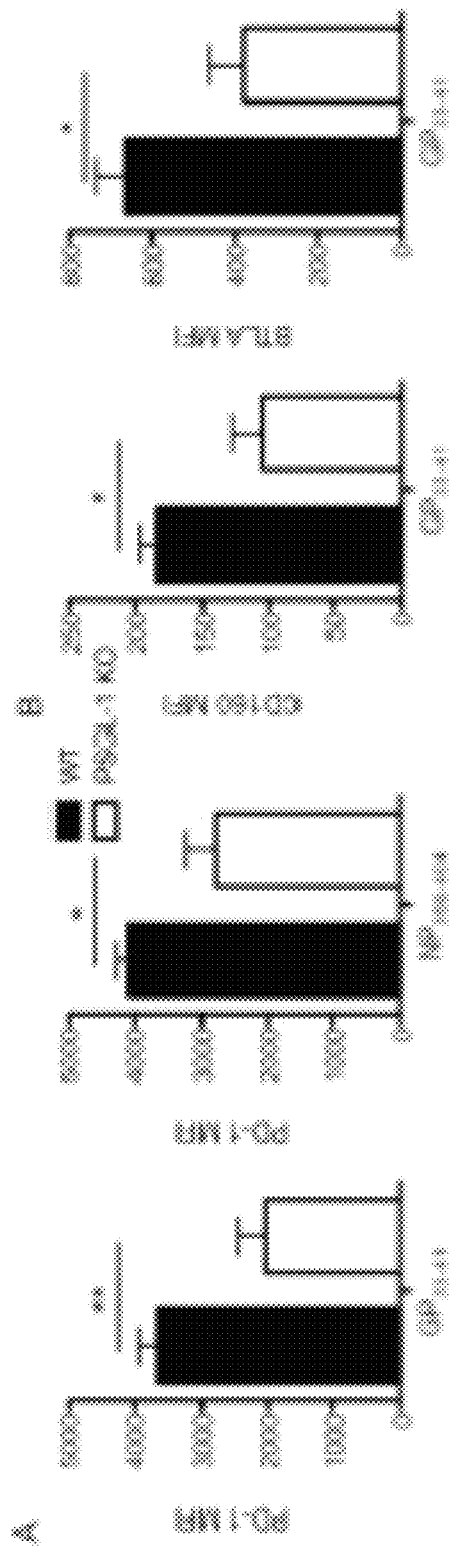
FIGS. 17A-B show deceased inhibitory receptor expression of virus specific CD8+ T cells. (A-B) Virus specific T cells were assessed from levels of PD-1 (A) and CD60 and BTLA (B).
Figures 18A, 18B, 18C:
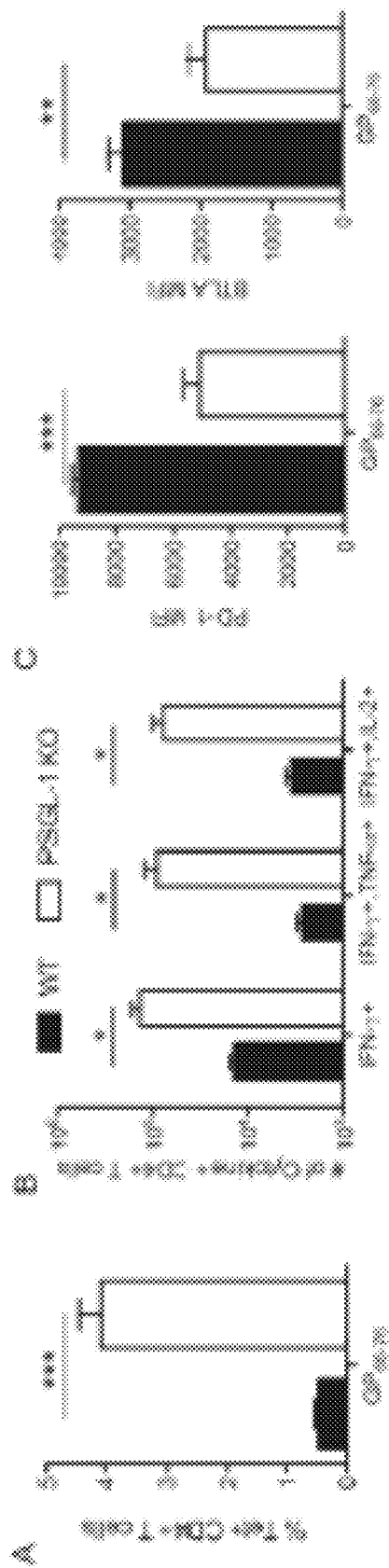
FIGS. 18A-C show PSGL-1 KO CD4+ T cells display improved survival and function with decreased inhibitory receptor expression. (A-C) the frequencies (A), cytokine responses (B) and PD-1 and BTLA levels (C) were measured on 8 dpi
Figures 19A, 19B:
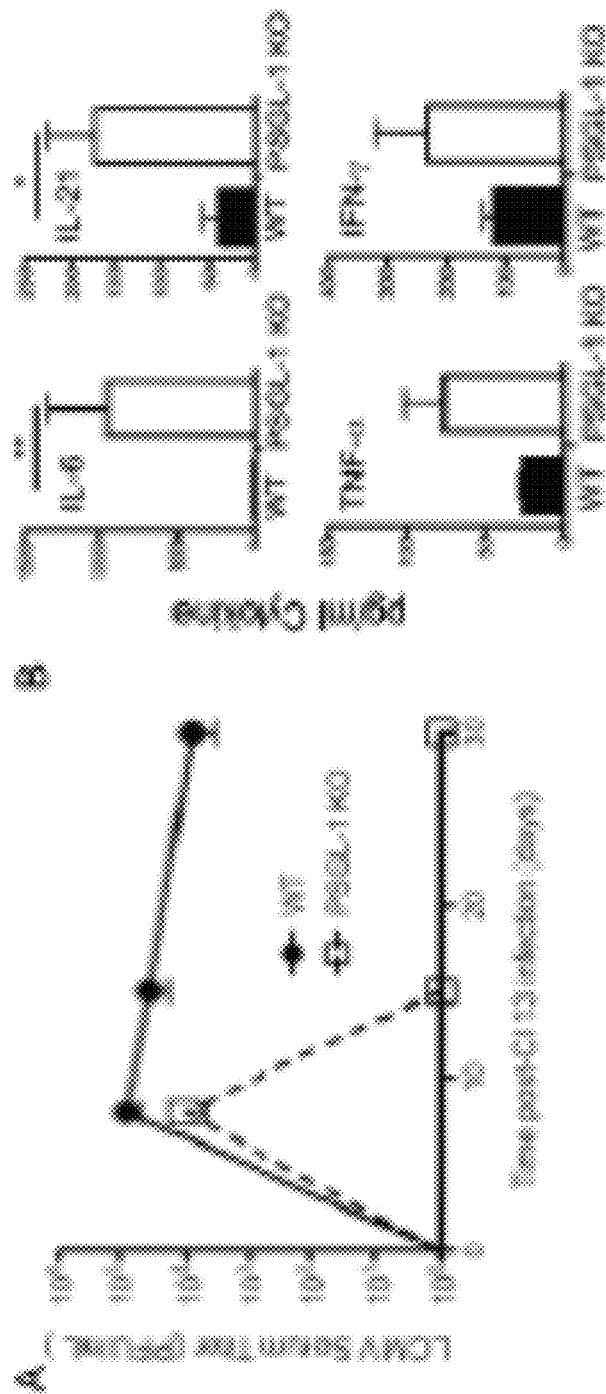
FIGS. 19A-B show PSGL-1 KO mice clear chronic LCMV and have greater circulating inflammatory cytokines. (A) virus titers post infection. (B) cytokine levels on 8 dpi.
Figures 20A, 20B, 20C, 20D:
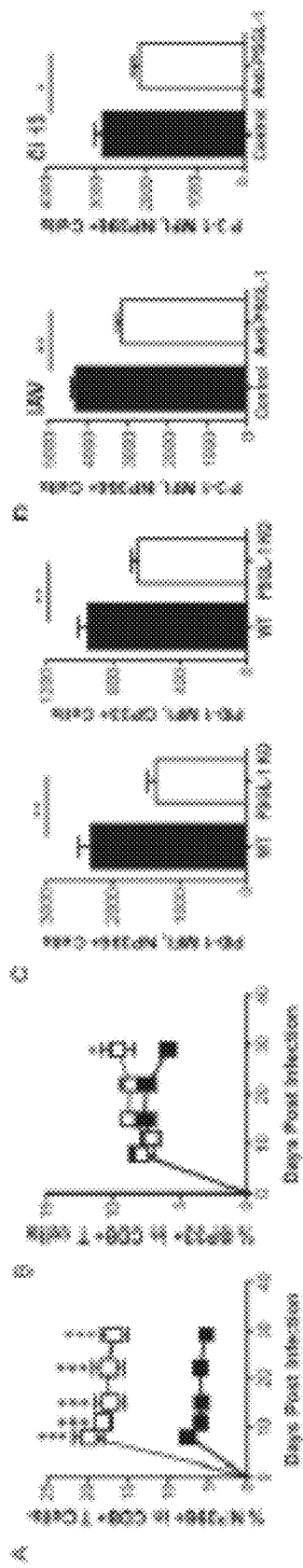
FIGS. 20A-D show T cell survival and PD-1 are modulated by PGSL-1 deficiency after response to virus infection and after PSGL-1 blockade. (A-D) Levels of $NP_{396-404}$ (A) and $GP_{33-41}$(B) specific CD8+ T cells analyzed post infection. (C) virus specific CD8+ T cells levels of PD-1 measured from WT and PSGL-1 KO mice. (D) PD-1 levels on IAV-specific $NP_{396-404}$ or LCMV specific $NP_{396-404}$ CD8+ T cells were measured on 8 dpi.

Exhausted CD8+ T cells are characterized by expression of multiple immune inhibitory receptors, notably PD-1, but also BTLA, CD160, LAG 3, TIM-3, and 2B4. It was found that reduced levels inhibitory receptors on CD8+ T cells was associated with improved function (FIG. 17) for both GP33-41 and NP396-404 specific T cells. Lower levels of 2B4 and LAG 3 were also found (not shown). CD4+ T cells responding to Cl13 in WT and PSGL-1 KO mice were analyzed. As shown for CD8+ T cells, there were greatly increased frequencies of virus-specific CD4+ T cells in KO mice (FIG. 18A) that were associated with better survival. Furthermore, virus-specific CD4+ T cells from PSGL-1 KO mice produced more cytokines than those from WT mice, and there were more polyfunctional cells as well (FIG. 18B). Greater function was associated with decreased expression of the inhibitory receptors, PD-1 and BTLA (FIG. 18C). These data indicate that PSGL-1 has a broader function than mediating migration in T cells and acts as a repressor of both CD8+ and CD4+ T cell responses. To determine whether improved T cell function and survival impacted the anti-viral response, viral clearance was measured. As shown in FIG. 17A, PSGL-1 deficiency enabled the Cl13 virus to be cleared. Greater levels of the cytokines IL-6, 1L-21, TNF-α, and IFN-γ were also detected in the sera of PSGL-1 KO mice compared to WT mice (FIG. 19B), thus providing a readout for an improved response. To further study PSGL-1 in anti-viral immunity, it was analyzed whether PD-1 expression levels after infection with the Armstrong LCMV strain, which is rapidly cleared by the immune system. Greater persistence of CD8+ T cells in this setting (FIG. 20) with an earlier and more pronounced effect of PD-1 on $NP_{396-404}$ (FIG. 20A) than $GP_{33-41}$ (FIG. 20B) virus specific CD8+ T cells was observed. For both clones, lower levels of PD-1 of PSGL-1 KO T cells were observed (FIG. 20C). To address whether levels of PD-1 on PSGL-1 can be targeted, an anti-PSGL-1 blocking antibody (4RA10) or control IgG was administered to WT mice after infection with influenza A virus (IAV) or with Cl13 LCMV. The anti-PSGL-1 treated groups had increased frequencies of virus specific CD8+ T cells (not shown) and these cells expressed lower levels of PD-1 than the controls (FIG. 20D). Together our findings indicate that PSGL-1 has a previously unknown general role in down modulating T cells responses.

Example 11

BRAFV600E PTEN Melanoma Model

Figures 21A, 21B:
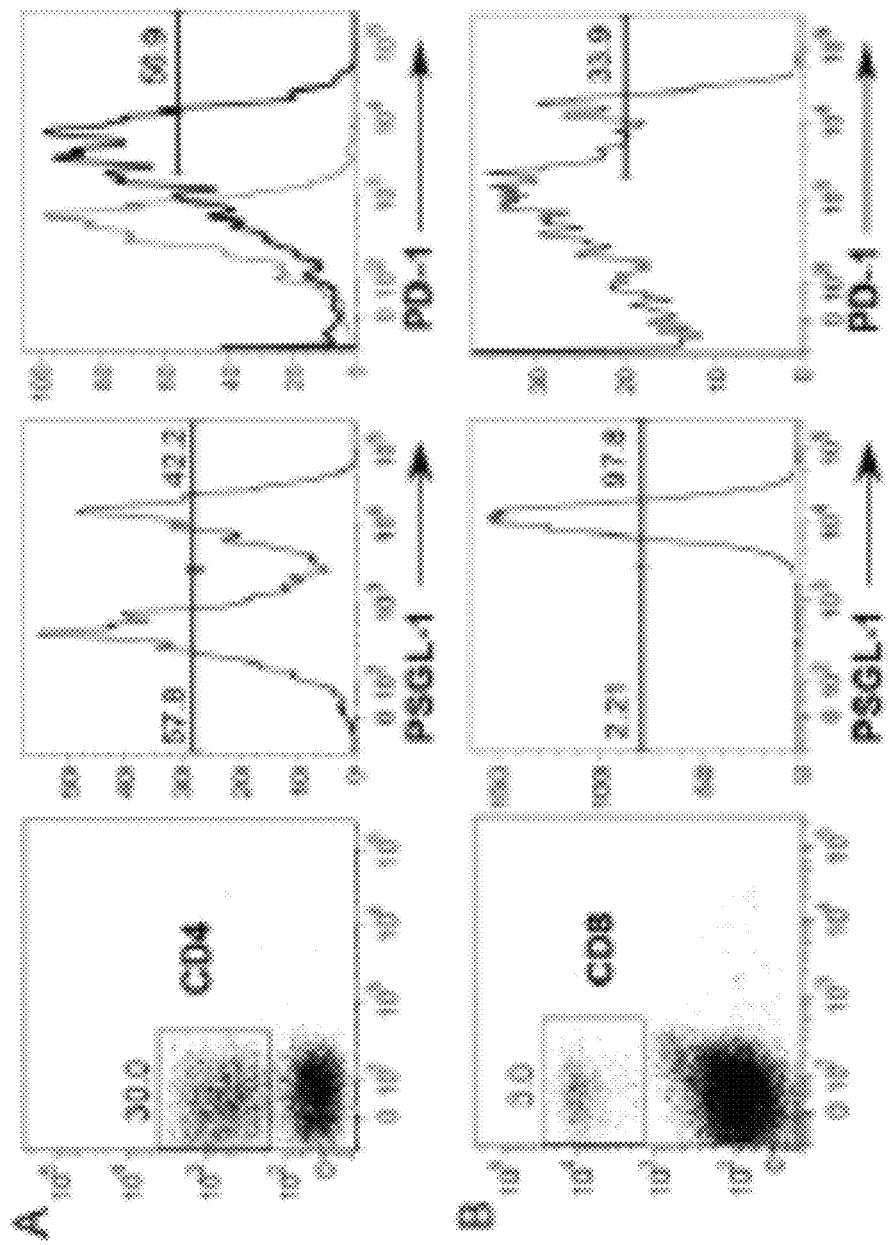
FIGS. 21A-B show PSGL-1 and PD-1 expression by T cells in tumor microenvironment. (A) frequency of CD4+ cells (left), their expression of PSGL-1 (middle) and expression of PD-1 by PSGL-110 cells versus high PSGL-1high cells (right). (B) frequency of CD8+ T cells (left), their high PSGL-1 expression (middle) and heterogeneous expression of PD-1.
Figures 22A, 22B:
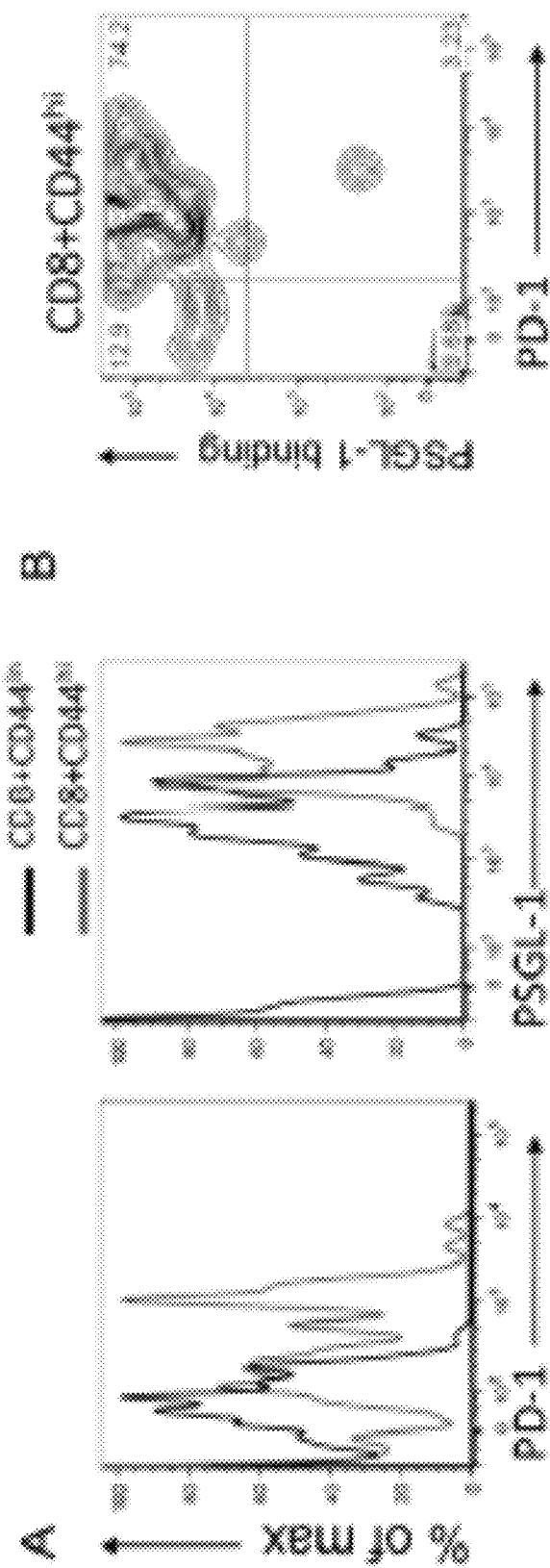
FIGS. 22A-B show PSGL-1 expression and PSGL-1 binding by CD8+ T cells in melanoma+ ears. (A) expression of PD-1 and PSGL-1 in $CD44^{hi}$ vs. $CD44^{lo}$ CD8+ T cells. (B) frequency of CD8+ T cells that have functional binding of PSGL-1.
Figures 23A, 23B:
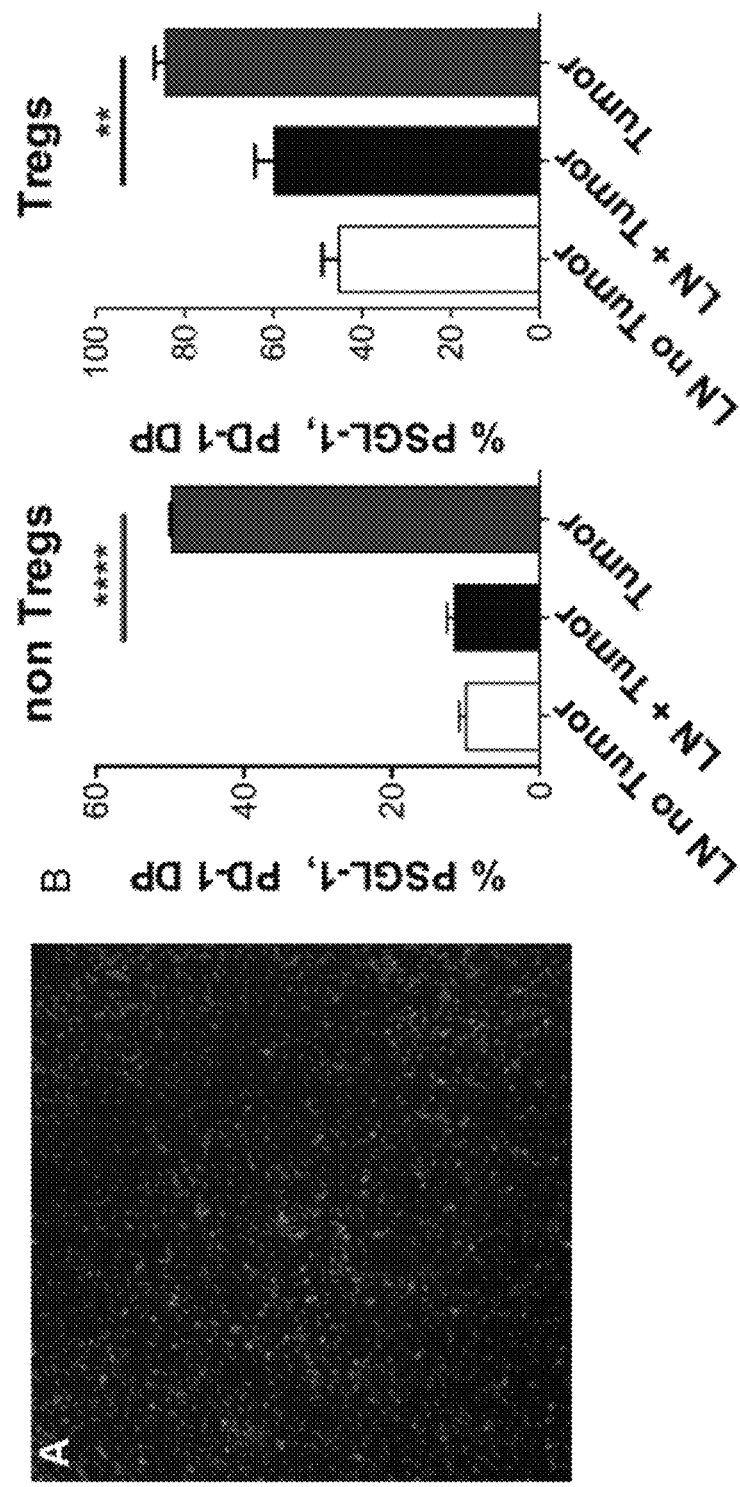
FIGS. 23A-B show CD3+ T cells in melanoma tumor, and the frequencies of CD4+ Tregs and CD4+ nonTregs. (A) CD3+ T cells monocuclear cells. (B) PSGL-1+, PD-1+ (double positive) CD4+ non Tregs (effector T cells) and Tregs with high frequency within the disrupted tumors by flow cytometry.
Figure 24:
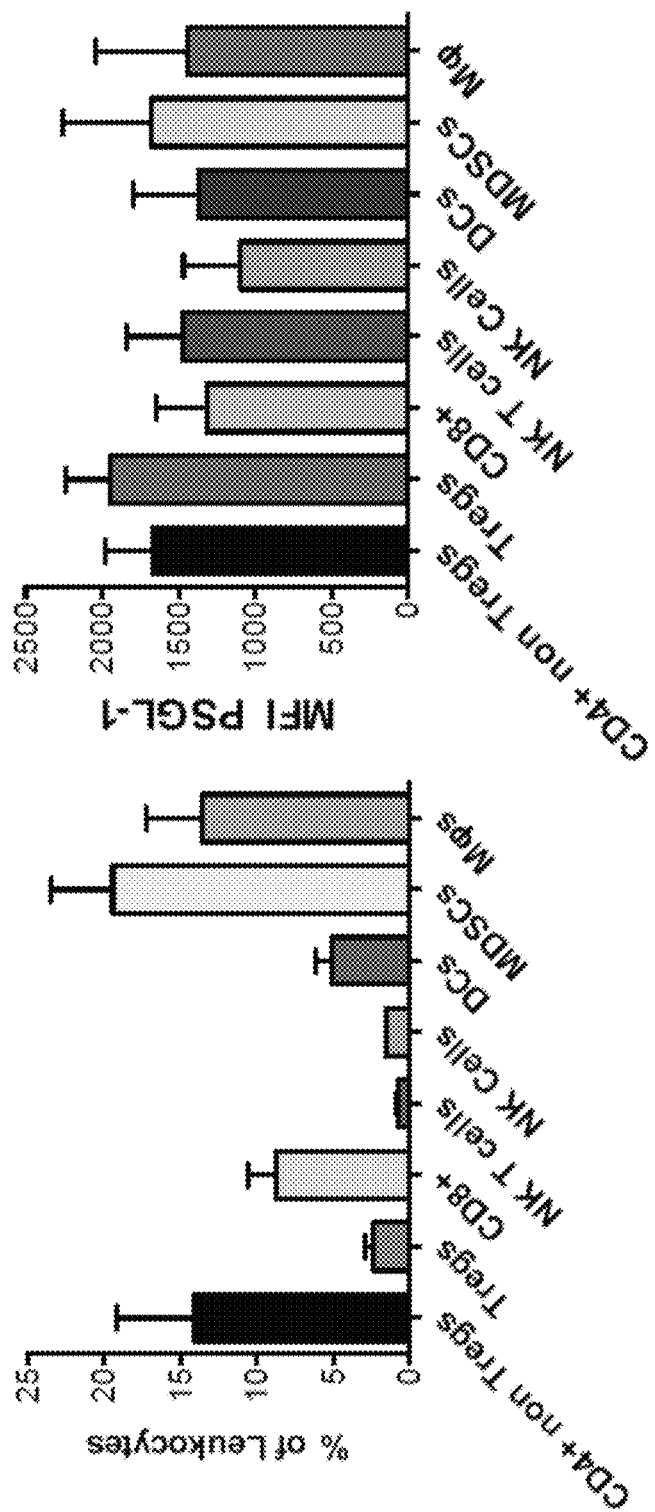
FIG. 24 shows the presence of immune cells in melanoma, and their expression of PSGL-1. (A) T cells (CD4+ non Tregs, Tregs, CD8+ cells), NK T cells, NK cells, dendritic cells (DCs, MHC II+, CD11c) myeloid derived suppressor cells (MDSC, Gr1+,CD11b) and macrophages (MΦ, F4/80+,CD11b+) identified within melanoma tumors. (B) these subsets of immune cells expressed PSGL-1.

One of the best currently available murine models of aggressive human melanoma is an inducible genetic model that combines the BRAFV600E mutation, which is present in ~65% of patients, with silencing of PTEN, a combination found in ~20% of patients. Cre/Lox induction of BRAFV600E and deletion of PTEN is temporarily controlled in melanocytes with activation of a melanocyte-tyrosinanse promoter, Try:CreER, by localized treatment of the skin with tamoxifen. There is 100% penetrance with pigmented lesions developing by 2 wks and metastatic disease by 1 mo. CD3+ T cells and CD45+ mononuclear cells within the skin-associated tumors were detected (data not shown). Tumors were analyzed by flow cytometry. Both CD4+ and CD8+ T cells were readily detected (FIG. 21A, B, left panels). PSGL-1 is expressed on ~1/2 the CD4+ cells, and it is these cells that have high PD-1 (FIG. 21A, middle, and right panels). The CD8+ T cells were exclusively PSGL-P, had mixed expression of PD-1 (FIG. 21B). Furthermore, in melanoma+ ears, increased PD-1 and PSGL-1 expression were detected on activated CD44+CD8+ T cells (FIG. 22A). These exhausted PD-1hi T cells also had functional PSGL-1 binding (FIG. 22B). These findings indicate that tumor-infiltrating CD8+ T cells have increased PD-1, PSGL-1 and PSGL-1 binding activity. In additional studies, melanoma was induced in mice by Cre/Lox induction of the BRAFV600E mutation and deletion of PTEN in melanocytes with activation of a melanocyte-tyrosinase promoter, Tyr::CreER, by localized treatment of the skin with tamoxifen. At 1 mo after treatment we observed CD3+ T cells monocuclear cells within (FIG. 23A), and PSGL-1+, PD-1+(double positive) CD4+ non Tregs (effector T cells) and Tregs with high frequency within the disrupted tumors by flow cytometry (FIG. 23B). By comparison, few T cells expressed both molecules in the skin draining LN of either tumor bearing mice or non tumor bearing mice. CD3+ T cells were found to be distributed throughout the melanoma (FIG. 23A), and both CD4+ non Tregs as well as Tre were detectable and coexpressed PD-1 and PSGL-1 (FIG. 23B). Additional studies of melanomas from these mice show that immune cells can be readily distinguished by flow cytometry, including CD8+ and CD4+ T cells, Tregs, MDSCs and DCs, NK cells, NK T cells, and macropphages (FIG. 24).

Example 12

To Identify PSGL-1 Expressing Cells and their Responses within Primary and Metastatic Melanoma Immune cell changes with melanoma development: The kinetics of tumor growth will be established and the development of infiltrates by 4 hydroxytamoxifen (4-HT) treatment of Tyr:CreER;Braf/Ptenlox/lox mice on the flank at 6 wks of age. Immunohistochemistry will be used to assess tumors at weekly intervals once tumors are detected, focusing in particular on CD44– and CD8+ T cells and their localization at the tumor margins vs infiltration into the tumors. For flow cytometry studies, the primary melanoma and draining LN will be compared and changes assessed that occur after metastasis to other skin sites, LN, and lungs. PSGL-1 and inhibitory receptor expression (PD-1, Tim-3, Lag-1, BTLA, CTLA-4, and CD160) will be analyzed on CD8+, CD4+ and FoxP3+ Tregs in the tumors, draining lymph nodes and nondraining lymph nodes, blood, spleen, and lungs with time after 4-HT treatment. Studies of the B16 melanoma model showed that tumor-specific CD84– T cells can be monitored using MHC Class I tetramers loaded with the peptide gp100$_{25-33}$ (KVPRNQDWL) of pmel-1, the mouse homologue of gp100$_{25-33}$ a structural component of the human melanosome matrix that is expressed by melanocytes as well malignant melanoma cells. This peptide is expressed by the melanomas induced in the BRAFV600E PTEN melanoma model. Therefore, to study tumor-specific T cell responses commercially available pmel-tetramers will be used. Whether there are changes in the frequencies or melanoma-specific CD8+ T cells, their expression levels of PSGL-1 will be addressed and whether they show differences from the overall CD8+ T cell population in inhibitory receptor expression. Intracellular staining (ICS) after anti-CD3 stimulation will be used to monitor the functions of CD4+ and CD8+ T cells by cytokine production (IL-2, IFN-γ, TNF-α), and pmel peptide restimulation will be used to assess cytokine production by tumor-specific CD8+ T cells. For CD8+ T cells. Cytotoxic activity by granzyme B staining will be tested as well as by degranulation by measuring CD107.

The immunosuppressive activity of Tregs by FoxP3 expression levels, which correlate with function (16), will be tested as well as 1L-10 and TGF-β production by ICS. The ratios of effector CD4+ and CD8+ T cells to Tregs will be evaluated in the melanomas and draining LN to determine changes that occur with time after the appearance of melanoma in the skin. Expansion of these populations will be examined by using BrdU administration in the drinking water, initiating treatment at 1, 2, 3, or 4 wks after 4-HT treatment, analyzing T cells in the melanomas, lymphoid tissues, and blood. To further interrogate the tumor microenvironment. The frequencies of DCs (MHC II+,CD11c+), MDSCs (Gr1+,CD11b+), and M4 (F4/80+,CD11b+) will be analyzed. To address function in these populations, ICS will be used to analyze production of IL-12 and 1L-10, which are associated with immunogenic vs tolerogenic DCs (17), and M1 vs M2 macrophages, respectively, whereas IL-10 distinguishes MDSCs.

Example 13

To Determine Whether Targeting PSGL-1 can Delay or Control the Development of Melanoma and its Metastases Impact of PSGL-1 on Melanoma.
Using a bone marrow chimera approach, whether PSGL-1 deficiency leads to changes in the functions of immune cells within the melanoma or in lymphoid compartment will be addressed. PSGL-1 deficiency will be created in hematopoietic cells by injecting PSGL-1 KO bone marrow into irradiated Tyr:CreER;Braf/Ptenloxilox mice and treat with 4-HT 8 wks later. Controls will receive WT bone marrow. Changes with respect to tumor growth and metastasis will be assessed, and in the frequencies and functions as well as inhibitory receptor expression on immune cells in the tumor microenvironment, lymphoid compartment, lungs and blood using histology and flow cytometry, focusing on the best readouts and time points defined in those studies. Evidence of autoimmunity/immunopathology by histology will be examined since deficiency or blocking of inhibitory receptors is associated with the development of inflammation.

Figures 25A, 25B, 25C, 25D, 25E, 25F:
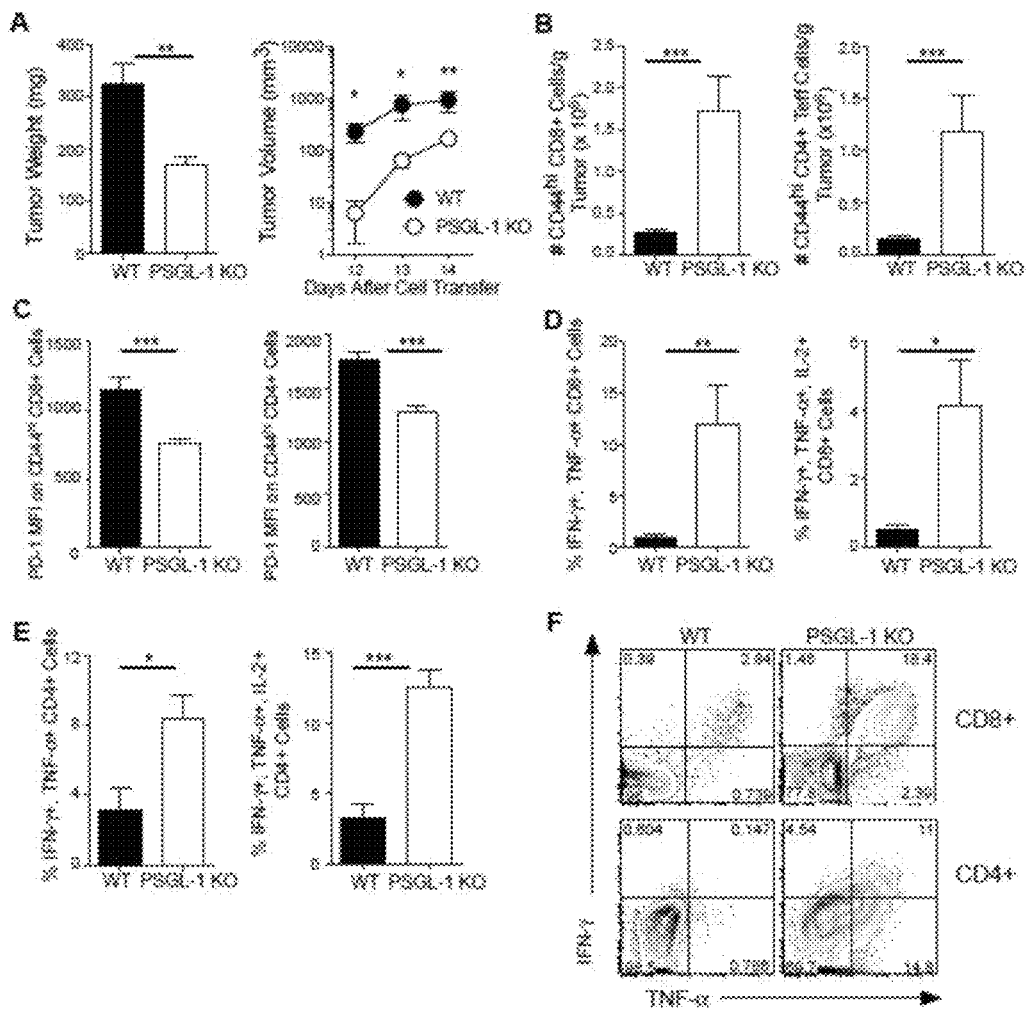
FIGS. 25A-F show the anti-tumor response of PSGL-1-deficient mice compared to WT mice. (A) tumor volume and weight. (B) the frequency of effector CD8+ and CD4+ T cells. (C) the expression of PD-1 by CD8+ and CD4+ T cells. (D-F) cytokine production by CD8+ and CD4+ T cells.

FIG. 25 shows enhanced anti-tumor T cell responses in PSGL-1-deficient mice. WT (black bars or black circles), and PSGL-1 KO (white bars or squares) received a subcutaneous injection of melanoma cells (Yumm 1.5. Tumor weight on d14 and volume to day 12 post-injection) (A). The absolute number of effector CD8+(left) and CD4+(right) T cells per gram of tumor (B). PD-1 expression on effector T cells (C). Cyokine production by CD4+ (D) and CD8+ T cells (E). Representative cytokine staining is shown in (F).

To address T cell intrinsic effects of PSGL-1 deficiency, two approaches will be used. First, chimeras where PSGL-1 will be deleted exclusively in T cells will be generated for comparison to chimeras with allelically marked WT cells. To achieve this, lethally irradiated Tyr:CreER;Braf/Ptenlox/lox mice (Thy1.2, CD45.2) are reconstituted with a 80:20 ratio of TCR WS KO (CD45.2):PSGL-1 KO bone marrow cells (Thy1.1,CD45.2). The mice will be treated with 4-HT 8 wks later and the development and metastases of the tumors and responses of the T cells will be evaluated. As a second approach, pmel Tg mice will be bred to PSGL-1 Thy1.1, CD45.2 KO mice CD8+ T cells isolated from these or WT pmel Tg mice (Thy1.1,CD45.2) will be injected into Tyr: CreER;Braf/Pten lox/lox (Thy 1.2, Ly 5.2) in an optimized dose. As an alternative, we have used a melanoma cell line, (Yumm 1.5) derived from an induced primary melanoma. Tumor cells were implanted s.c. in a dose of 5×10$^5$ (right flank) into WT or PSGL-1 deficient mice. In FIG. 24, tumor growth was monitored by volume and weight (A), and the frequencies of effector CD8+ and CD4+ T cells were determined (B). PSGL-1 deficient mice had smaller tumors and contained greater numbers of T cells. The T cells expressed lower levels of PD-1 (C) and were more functional as measured by cytokine production (D-F).

Immunotherapeutic inhibition PSGL-1 function. Whether blocking PSGL-1 with an agonist mAb (4RA10) or a recombinant PSGL-1 Fc fusion protein can control growth and/or metastases of melanoma with reversal of T cell dysfunction will be determined. These reagents will be tested as a treatment of the primary melanoma as well as after metastasis has occurred. For the primary tumor, local injection of mAb into the tumor will be compared with systemic treatment. For local treatment, a starting dose of 100 µg of anti-PSGL-1 or control IgG at the time of primary tumor detection will be used. For systemic treatment 300 µg/mAb/dose will be injected i.p. with treatment every other day for 5 days and will follow the animals tumor growth and skin metastases. At 1 mo, the animals will be examined for pmel-tetramer+ CD8+ T cells, their surface expression of inhibitory receptors, and their responses in the blood, spleen, LN, and, as indicated, tumors. The effects of initiating systemic mAb treatment will be examined at 1, 2, 3 or 4 wks after detection of the primary tumor to address whether anti-PSGL-1 can impact the anti-tumor response with progressing disease. As a second strategy to block PSGL-1, PSGL-1 Fc will be administered with human Ig as the control. The mAb and fusion protein levels will be assessed in the serum every 3-4 days by ELISA to determine the 1/2 lives, and to address whether there are changes in T cell phenotype and/or responses with the decay of these reagents. Levels of IL-6, IL-21, TNF-α, and IFN-γ will be measured in the sera at weekly intervals after the initiation of therapy to determine if changes in cytokine levels occur, and whether there is an association with improved anti-T cell tumor activity or tumor resolution.

Although the invention has been described with reference to the above examples, it will be understood that modifications and variations are encompassed within the spirit and scope of the invention. Accordingly, the invention is limited only by the following claims.

What is claimed is:

1. A method of treating a T cell mediated disease or disorder comprising administering a P-selectin glycoprotein ligand-1 (PSGL-1) modulator to a subject in need thereof, wherein the modulator is a PSGL-1 antagonist, and wherein the T cell mediated disease or disorder is an infectious disease, an inflammatory disorder, or melanoma.

2. The method of claim 1, wherein the infectious disease is selected from the group consisting of Botulism, Bubonic plague, Calicivirus infection (Norovirus and Sapovirus), Chickenpox, *Chlamydia*, Cholera, *Clostridium difficile* infection, Common cold (Acute viral rhinopharyngitis; Acute coryza), Creutzfeldt-Jakob disease (CJD), Dengue fever, Diphtheria, Ebola hemorrhagic fever, Gonorrhea, Hand, foot, and mouth disease (HFMD), *Helicobacter pylori* infection, Hepatitis A, Hepatitis B, Hepatitis C, Hepatitis D, Hepatitis E, Herpes simplex, human immunodeficiency virus (HIV), Human papillomavirus (HPV) infection, Epstein-Barr Virus, Infectious Mononucleosis (Mono), Influenza (flu), Legionellosis (Legionnaires' disease), Leprosy, Lyme disease (Lyme borreliosis), Malaria, Marburg hemorrhagic fever (MHF), Measles, Middle East respiratory syndrome (MERS), Meningitis, Mumps, Pertussis (Whooping cough), Plague, Progressive multifocal leukoencephalopathy, Rabies, Rhinovirus infection, Rocky Mountain spotted fever (RMSF), Rubella, *Salmonellosis*, SARS (Severe Acute Respiratory Syndrome), Scabies, Sepsis, Shigellosis (Bacillary dysentery), Shingles (Herpes zoster), Smallpox (Variola), Syphilis, Tetanus (Lockjaw), Tuberculosis, Typhoid Fever, Valley fever, Viral pneumonia, West Nile Fever, and Yellow fever.

3. The method of claim 1, wherein the PSGL-1 antagonist is an antibody, a small molecule, a protein, a fusion protein, or a nucleic acid.

4. The method of claim 3, wherein the antibody is a monoclonal antibody, chimeric antibody, human antibody, or humanized antibody.

5. The method of claim 2, wherein viral clearance is increased.

6. A method of eliciting a T cell response comprising administering a P-selectin glycoprotein ligand-1 (PSGL-1) modulator to a subject in need thereof, wherein the PSGL-1 modulator is a PSGL-1 antagonist, and wherein the subject has an infectious disease, an inflammatory disorder, or melanoma.

7. The method of claim 6, wherein the PSGL-1 antagonist is an antibody, a small molecule, a protein, a fusion protein, or a nucleic acid.

8. The method of claim 7, wherein the antibody is a monoclonal antibody, chimeric antibody, human antibody, or humanized antibody.

* * * * *